United States Patent
Goldshtein et al.

(10) Patent No.: US 10,874,349 B2
(45) Date of Patent: Dec. 29, 2020

(54) DEPLOYING AND FIXATING AN IMPLANT ACROSS AN ORGAN WALL

(71) Applicant: VECTORIOUS MEDICAL TECHNOLOGIES LTD, Tel Aviv (IL)

(72) Inventors: Oren Goldshtein, Nahariya (IL); Yair Levi, Haifa (IL); Boaz Harari, Ganey Tikva (IL)

(73) Assignee: VECTORIOUS MEDICAL TECHNOLOGIES LTD., Tel Aviv (IL)

( * ) Notice: Subject to any disclaimer, the term of this patent is extended or adjusted under 35 U.S.C. 154(b) by 311 days.

(21) Appl. No.: 15/566,329

(22) PCT Filed: May 7, 2016

(86) PCT No.: PCT/IB2016/052617
§ 371 (c)(1),
(2) Date: Oct. 13, 2017

(87) PCT Pub. No.: WO2016/178197
PCT Pub. Date: Nov. 10, 2016

(65) Prior Publication Data
US 2018/0098772 A1    Apr. 12, 2018

Related U.S. Application Data

(60) Provisional application No. 62/157,991, filed on May 7, 2015, provisional application No. 62/306,134, filed on Mar. 10, 2016.

(51) Int. Cl.
*A61B 17/00* (2006.01)
*A61B 5/00* (2006.01)
(Continued)

(52) U.S. Cl.
CPC .......... *A61B 5/6869* (2013.01); *A61B 5/0031* (2013.01); *A61B 5/0215* (2013.01);
(Continued)

(58) Field of Classification Search
CPC ..... A61B 5/6869; A61B 5/076; A61B 5/6884; A61B 5/686; A61B 5/0031;
(Continued)

(56) References Cited

U.S. PATENT DOCUMENTS 3,264,861 A    8/1966  Miles
4,127,110 A    11/1978 Bullara
(Continued)

FOREIGN PATENT DOCUMENTS

AL    2 986 252 A1    2/2016
CN    103239791 A     8/2013
(Continued)

OTHER PUBLICATIONS

WIPO, U.S. International Search Authority, International Search Report and Written Opinion dated Oct. 19, 2016 in International Patent Application No. PCT/IB2016/052617, 16 pages.
(Continued)

*Primary Examiner* — Vy Q Bui
(74) *Attorney, Agent, or Firm* — Kligler & Associates Patent Attorneys Ltd

(57) ABSTRACT

Implant deployment device for delivering and deploying an implant. Includes: deployment device body for pushing implant in subject's blood vessel, across an interatrial septum and into subject's heart left atrium; and a handle operatively connected to deployment device and having controls assigned to selectively operate positioning of the deployment device, to facilitate determining compression extent of an implant body, and detaching of deployment device from the implant. Also disclosed are: a method for
(Continued)

fixating an elongated implant across an organ wall in a subject's body, and a method for sealing a wall opening in a septal wall in a subject's body.

17 Claims, 27 Drawing Sheets

(51) Int. Cl.
 *A61B 5/0215* (2006.01)
 *A61B 17/12* (2006.01)
 *A61B 5/07* (2006.01)

(52) U.S. Cl.
 CPC .............. *A61B 5/076* (2013.01); *A61B 5/686* (2013.01); *A61B 5/6884* (2013.01); *A61B 17/0057* (2013.01); *A61B 17/12122* (2013.01); *A61B 17/12172* (2013.01); *A61B 2017/00477* (2013.01); *A61B 2017/00606* (2013.01); *A61B 2017/00623* (2013.01); *A61B 2017/12054* (2013.01)

(58) Field of Classification Search
 CPC .............. A61B 17/0057; A61B 5/0215; A61B 17/12122; A61B 2017/00477; A61B 2017/00606; A61B 2017/00623; A61B 2017/12054; A61B 2017/00411; A61B 2017/00592; A61B 2017/00575; A61B 2017/00221; A61B 2017/00022
 USPC ................ 606/1, 27, 45, 151, 185, 200, 213
 See application file for complete search history.

(56) References Cited

U.S. PATENT DOCUMENTS

| | | |
|---|---|---|
| 4,206,761 A | 6/1980 | Cosman |
| 4,237,900 A | 12/1980 | Schulman et al. |
| 4,256,094 A | 3/1981 | Kapp et al. |
| 4,377,851 A | 3/1983 | McNamara |
| 4,432,372 A | 2/1984 | Monroe |
| 4,519,401 A | 5/1985 | Ko et al. |
| 4,743,836 A | 5/1988 | Grzybowski et al. |
| 4,791,934 A | 12/1988 | Brunnett |
| 4,881,939 A | 11/1989 | Newman |
| 5,105,190 A | 4/1992 | Kip et al. |
| 5,480,412 A | 1/1996 | Mouchawar et al. |
| 5,493,470 A | 2/1996 | Zavracky et al. |
| 5,514,171 A | 5/1996 | Hoegnelid et al. |
| 5,564,434 A | 10/1996 | Halperin et al. |
| 5,725,552 A | 3/1998 | Kotula |
| 5,942,692 A | 8/1999 | Haase et al. |
| 6,015,386 A | 1/2000 | Kensey et al. |
| 6,025,725 A | 2/2000 | Gershenfeld et al. |
| 6,051,853 A | 4/2000 | Shimada et al. |
| 6,111,520 A | 8/2000 | Allen et al. |
| 6,113,553 A | 9/2000 | Chubbuck |
| 6,275,681 B1 | 8/2001 | Vega et al. |
| 6,309,350 B1 | 10/2001 | VanTassel et al. |
| 6,389,371 B1 | 5/2002 | Tsuchiya et al. |
| 6,409,674 B1 | 6/2002 | Brockway et al. |
| 6,622,041 B2 | 9/2003 | Terry, Jr. et al. |
| 6,667,725 B1 | 12/2003 | Simons et al. |
| 6,772,070 B2 | 8/2004 | Gilmanshin et al. |
| 6,926,670 B2 | 8/2005 | Rich et al. |
| 6,936,053 B1 | 8/2005 | Weiss |
| 7,086,270 B2 | 8/2006 | Weinberg et al. |
| 7,149,587 B2 | 12/2006 | Wardle et al. |
| 7,216,048 B2 | 5/2007 | Wang et al. |
| 7,256,695 B2 | 8/2007 | Hamel et al. |
| 7,317,951 B2 * | 1/2008 | Schneider .......... A61B 17/0057 606/213 |
| 7,335,161 B2 | 2/2008 | Von Arx et al. |
| 7,413,547 B1 | 8/2008 | Lichtscheidl et al. |
| 7,425,749 B2 | 9/2008 | Hartzell et al. |
| 7,509,169 B2 | 3/2009 | Eigler et al. |
| 7,515,971 B1 | 4/2009 | Doan |
| 7,628,054 B2 | 12/2009 | Hajishah et al. |
| 7,634,319 B2 | 12/2009 | Schneider et al. |
| 7,635,338 B2 | 12/2009 | Eide |
| 7,647,831 B2 | 1/2010 | Corcoran et al. |
| 7,677,107 B2 | 3/2010 | Nunez et al. |
| 7,678,123 B2 | 3/2010 | Chanduszko |
| 7,684,872 B2 | 3/2010 | Carney et al. |
| 7,686,768 B2 | 3/2010 | Bodecker et al. |
| 7,762,138 B2 | 7/2010 | Zdeblick et al. |
| 7,860,579 B2 | 12/2010 | Goetzinger et al. |
| 7,899,550 B1 | 3/2011 | Doan et al. |
| 8,021,307 B2 | 9/2011 | White et al. |
| 8,118,749 B2 | 2/2012 | White et al. |
| 8,154,389 B2 | 4/2012 | Rowland et al. |
| 8,285,204 B2 | 10/2012 | Martin |
| 8,353,841 B2 | 1/2013 | White et al. |
| 8,355,777 B2 | 1/2013 | White et al. |
| 8,432,265 B2 | 4/2013 | Rowland et al. |
| 8,493,187 B2 | 7/2013 | Rowland et al. |
| 8,894,582 B2 | 11/2014 | Nunez et al. |
| 8,992,545 B2 * | 3/2015 | Cahill ................ A61B 17/0057 606/108 |
| 9,320,597 B2 | 4/2016 | Savage et al. |
| 2001/0018596 A1 | 8/2001 | Selmon et al. |
| 2002/0045921 A1 | 4/2002 | Wolinsky et al. |
| 2002/0072656 A1 | 6/2002 | Vantassel et al. |
| 2002/0077556 A1 | 6/2002 | Schwartz |
| 2002/0120200 A1 | 8/2002 | Brockway et al. |
| 2002/0123760 A1 | 9/2002 | Amplatz |
| 2003/0097073 A1 | 5/2003 | Bullister et al. |
| 2003/0139677 A1 | 7/2003 | Fonseca et al. |
| 2004/0092985 A1 | 5/2004 | Parihar et al. |
| 2004/0103906 A1 | 6/2004 | Schulman et al. |
| 2004/0113790 A1 | 6/2004 | Hamel et al. |
| 2005/0004644 A1 | 1/2005 | Kelsch et al. |
| 2005/0043759 A1 | 2/2005 | Chanduszko |
| 2005/0065589 A1 | 3/2005 | Schneider et al. |
| 2005/0088184 A1 | 4/2005 | Burdick et al. |
| 2005/0267523 A1 | 12/2005 | Devellian et al. |
| 2005/0288596 A1 | 12/2005 | Eigler et al. |
| 2006/0116572 A1 | 6/2006 | Case |
| 2006/0161364 A1 | 7/2006 | Wang et al. |
| 2006/0206178 A1 | 9/2006 | Kim |
| 2006/0229488 A1 | 10/2006 | Ayre et al. |
| 2006/0287602 A1 | 12/2006 | O'Brien et al. |
| 2007/0049980 A1 | 3/2007 | Zielinski et al. |
| 2007/0049984 A1 | 3/2007 | Osypka |
| 2007/0118038 A1 | 5/2007 | Bodecker et al. |
| 2007/0135826 A1 | 6/2007 | Zaver et al. |
| 2007/0142727 A1 | 6/2007 | Zhang et al. |
| 2007/0179583 A1 | 8/2007 | Goetzinger et al. |
| 2007/0232898 A1 | 10/2007 | Huynh et al. |
| 2007/0255144 A1 | 11/2007 | Tulkki et al. |
| 2007/0261496 A1 | 11/2007 | Jonsson et al. |
| 2007/0293779 A1 | 12/2007 | Bardy |
| 2008/0004673 A1 | 1/2008 | Rossing et al. |
| 2008/0033527 A1 | 2/2008 | Nunez et al. |
| 2008/0045242 A1 | 2/2008 | Dekock et al. |
| 2008/0051863 A1 | 2/2008 | Schneider et al. |
| 2008/0064966 A1 | 3/2008 | Brockway et al. |
| 2008/0092663 A1 | 4/2008 | Corcoran et al. |
| 2008/0139959 A1 | 6/2008 | Miethke et al. |
| 2008/0154101 A1 | 6/2008 | Jain et al. |
| 2008/0269573 A1 | 10/2008 | Najafi et al. |
| 2008/0281212 A1 | 11/2008 | Nunez et al. |
| 2009/0005859 A1 | 1/2009 | Keilman |
| 2009/0013791 A1 | 1/2009 | Zdeblick et al. |
| 2009/0024042 A1 | 1/2009 | Nunez et al. |
| 2009/0030291 A1 | 1/2009 | O'Brien et al. |
| 2009/0036754 A1 | 2/2009 | Pons et al. |
| 2009/0069648 A1 | 3/2009 | Irazoqui et al. |
| 2009/0093729 A1 | 4/2009 | Zhang et al. |
| 2009/0192381 A1 | 7/2009 | Brockway et al. |
| 2009/0275924 A1 | 11/2009 | Lattanzio et al. |
| 2009/0281520 A1 | 11/2009 | Highley et al. |
| 2009/0299216 A1 | 12/2009 | Chen et al. |

(56) References Cited

U.S. PATENT DOCUMENTS

| | | |
|---|---|---|
| 2010/0179449 A1 | 7/2010 | Chow et al. |
| 2010/0179618 A1 | 7/2010 | Marnfeldt et al. |
| 2010/0249756 A1 | 9/2010 | Koh |
| 2010/0280330 A1 | 11/2010 | Samuelsson et al. |
| 2011/0021887 A1 | 1/2011 | Crivelli et al. |
| 2011/0040206 A1 | 2/2011 | Burger et al. |
| 2011/0043336 A1 | 2/2011 | Gueorguiev |
| 2011/0133894 A1 | 6/2011 | Hennig et al. |
| 2011/0160560 A1 | 6/2011 | Stone |
| 2011/0264217 A1 | 10/2011 | Qureshi |
| 2011/0303229 A1 | 12/2011 | Najafi et al. |
| 2012/0022507 A1 | 1/2012 | Najafi et al. |
| 2012/0078124 A1 | 3/2012 | White et al. |
| 2012/0319862 A1 | 12/2012 | Nagy et al. |
| 2013/0197571 A1 | 8/2013 | Hariton et al. |
| 2013/0215979 A1 | 8/2013 | Yakovlev et al. |
| 2013/0222153 A1 | 8/2013 | Rowland et al. |
| 2013/0233086 A1 | 9/2013 | Besling et al. |
| 2014/0028467 A1 | 1/2014 | Nagy et al. |
| 2014/0155710 A1 | 6/2014 | Rowland et al. |
| 2014/0213915 A1 | 7/2014 | Doan et al. |
| 2014/0306807 A1 | 10/2014 | Rowland et al. |
| 2014/0343601 A1 | 11/2014 | Abbott et al. |

FOREIGN PATENT DOCUMENTS

| | | |
|---|---|---|
| EP | 2 667 771 A2 | 12/2013 |
| KR | 1020040060577 A | 7/2004 |
| WO | 2005092203 A1 | 10/2005 |
| WO | WO 2006/042280 A2 | 4/2006 |
| WO | WO 2008/042229 A2 | 4/2008 |
| WO | WO 2008/127525 A2 | 10/2008 |
| WO | WO 2009/097485 A2 | 8/2009 |
| WO | WO 2011/053246 A2 | 5/2011 |
| WO | WO 2012/078861 A2 | 6/2012 |
| WO | WO 2012/090206 A2 | 7/2012 |
| WO | WO 2014/006471 A2 | 1/2014 |
| WO | WO 2014/145012 A2 | 9/2014 |
| WO | WO 2014/170771 A2 | 10/2014 |

OTHER PUBLICATIONS

Cleven, N. J. et al; "A Novel Fully Implantable Wireless Sensor System for Monitoring Hypertension Patients", IEEE Transactions on Biomedical Engineering vol. 59, No. 11, Nov. 2012, pp. 3124-3130.

Jiang, Guangqiang; "Design challenges of implantable pressure monitoring system", Frontiers of Neuroscience, vol. 4, Art. 29, 2010, pp. 1-4.

Simons, Rainee N. et al; "Spiral chip implantable radiator and printed loop external receptor for RF telemetry in bio-sensor systems", In Radion and Wireless Conference 2004, IEEE, 9 pages.

Simons, Rainee N. et al; "Wearable wireless telemetry system for implantable bio-MEMS sensors", In Engineering in Medicine and Biology Society Conference, 2006, IEEE, 10 pages.

Olivo, Jacopo et al; "Electronic Implants: PowerDelivery and Management", Design, Automation&Test in Europe Conference &Exhibition, 2013, IEEE, Mar. 18, 2013, pp. 1540-1545.

Coosemans, J. et al.; "An autonomous bladder pressure monitoring system", Katholike Universiteit Leuven, Department ESAT-MICAS, Kasteelpark Arenberg, Belgium, Sensors ans Actuators A: Physical, Elsevier BV, vol. 123-124, Sep. 23, 2005, pp. 155-161.

Dai, Ching-Liang et al., "Capacitive Micro Pressure Sensor Integrated with a Ring Oscillator Circuit on Chip", Sensors 2009, vol. 9, Chapter 12, pp. 10158-10170, Jan. 1, 2009.

Yameogo, Pierre et al., "Self calibrating pressure sensor for biomedical applications", IEEE Sensors Conference, pp. 691-694, Oct. 25-28, 2009.

Mandal, Soumyajit et al., "Power-Efficient Impedance-Modulation Wireless Data Links for Biomedical Implants", IEEE Transactions on Biomedical Circuitsand Systems, vol. 2, No. 4, pp. 301-315, Dec. 4, 2008.

Bradford, Bryce et al., "Wireless Power and Data Transmission for a Pressure Sensing Medical Implant", Proceedings BMT 2010, Rostock, Germany, 4 pages, Oct. 6-8, 2010.

Maxim Integrated Products, "Approaches for Compensating Span and Offset in Pressure Sensors", Application Note 743, Mar. 27, 2001.

U.S. Appl. No. 15/566,296 office action dated Feb. 6, 2020.

CN Patent Application # 201680025331.8 Office Action dated Dec. 4, 2019.

U.S. Appl. No. 15/566,296 Office Action dated Jul. 23, 2020.

\* cited by examiner

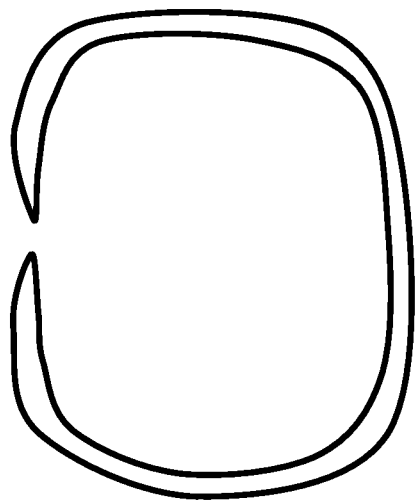
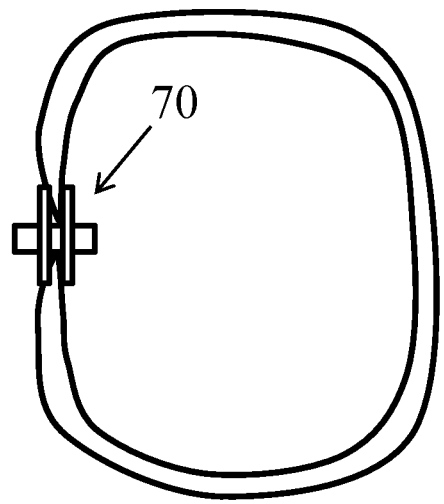
FIG. 5A                FIG. 5B
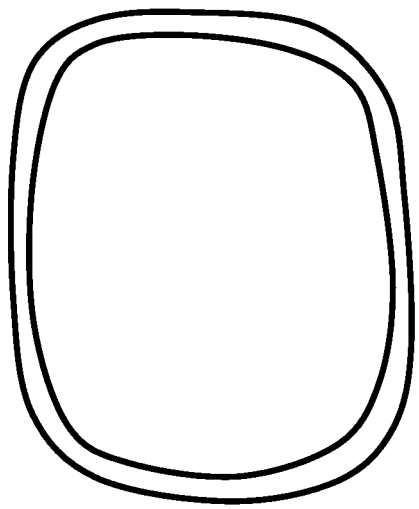
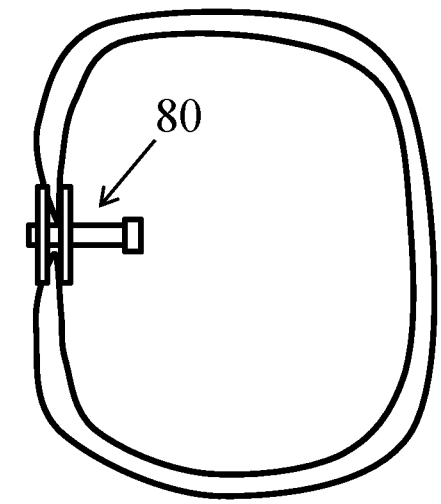
FIG. 6A                FIG. 6B

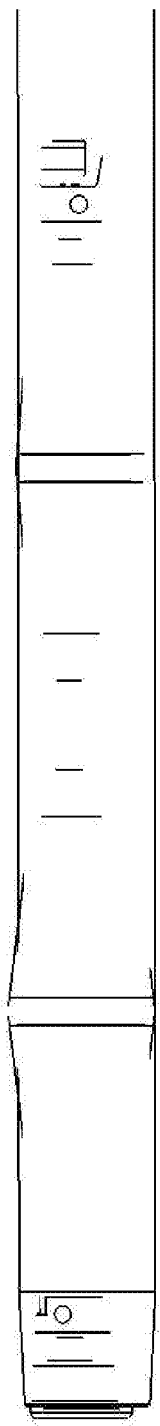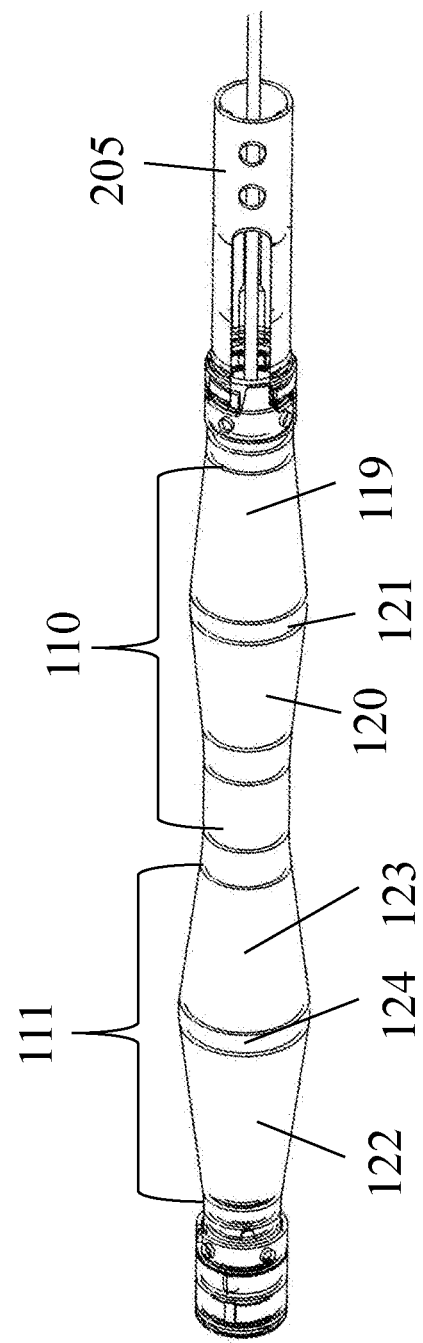
FIG. 8D
FIG. 8E

DEPLOYING AND FIXATING AN IMPLANT ACROSS AN ORGAN WALL

RELATED APPLICATIONS

This application is the U.S. National Phase of and claims priority to International Patent Application No. PCT/IB2016/052617, International Filing Date May 7, 2016, entitled "DEPLOYING AND FIXATING AN IMPLANT ACROSS AN ORGAN WALL", which claims benefit of U.S. Provisional Application Ser. No. 62/157,991 filed May 7, 2015, entitled "MECHANICAL DESIGN, PACKAGING AND DELIVERY FOR A SENSORY IMPLANT", and of U.S. Provisional Application Ser. No. 62/306,134 filed Mar. 10, 2016, entitled "HEART IMPLANT WITH SEPTUM GRIPPER", the contents of the preceding documents are incorporated herein by reference in their entireties.

FIELD OF THE INVENTION

The present invention, in some embodiments thereof, relates to implant deployment devices and methods for delivering and deploying an implant in a subject, and more particularly, but not exclusively, to an implant deployment device, and method using thereof, for deploying and fixating an implant across an organ wall in a subject. Exemplary embodiments of the present invention also relate to a method for sealing a wall opening in a septal wall in a subject's body.

BACKGROUND OF THE INVENTION

Pressure measurements in one or more chambers of the heart may be used as indicators for several cardiac conditions. By measuring cardiac pressure, abnormal events can be detected and the appropriate treatment methodology may be applied to avoid otherwise deleterious cardiac conditions. For example, monitoring the left atrial pressure of congestive heart failure (CHF) patients is preferred for effectively diagnosing an abnormal change in left atrial pressure.

Proposed implants for sensing a pressure in heart atrium can be fixed to atrial wall (such as the atrial septum). Means are thus required for deploying and fixating the implant to atrial wall, while preferably diminishing or preventing short-term or/and long-term effects to implant's sensing or/and other capabilities due to local and surrounding potential disturbances. There is thus a need for sensory implants that could be safely and effectively implanted within the heart, and used for long-term, real time and reliable cardiac pressure measurements in right or/and the left atrium.

SUMMARY OF THE INVENTION

The present invention, in some embodiments thereof, relates to implant deployment devices and methods for delivering and deploying an implant in a subject, and more particularly, but not exclusively, to an implant deployment device, and method using thereof, for deploying and fixating an implant across an organ wall in a subject. Also disclosed are exemplary embodiments of a method for sealing a wall opening in a septal wall in a subject's body.

According to an aspect of some embodiments of the present invention, there is provided an implant deployment device for delivering and deploying an implant, the implant deployment device comprising: a deployment device body dimensioned, structured and configured to push the implant in a subject's blood vessel, across an interatrial septum and into a left atrium in subject's heart, the implant possesses a rigid implant body enclosed with a compressible tubular skirt, said deployment device body includes: an inner member with an inner connector at a distal end thereof, said inner connector is adapted to detachably connect to an inner connectee provided at a proximal end of said implant body, and an outer member with an outer connector at a distal end thereof, said outer connector is adapted to detachably connect to an outer connectee provided at a proximal end of said tubular skirt; and a handle operatively connected to proximal ends of said deployment device body inner and outer members and comprising controls assigned to selectively operate positioning of said outer connector longitudinally relative to said inner connector, to thereby facilitate: (i) determining extent of compression of said compressible tubular skirt along said implant body, (ii) detaching of said inner connector from said inner connectee, and (iii) detaching of said outer connector from said outer connectee separately from said detaching of said inner connector from said inner connectee.

According to some embodiments of the invention, the tubular skirt comprises a flexible gripping sleeve fixedly connected with distal end thereof to a distal periphery of said implant body and slidably connected with said proximal end thereof to said implant body along a path extending proximally to said distal periphery, said gripping sleeve is compressible into a gripping form with sufficient force to maintain said implant body aligned within said left atrium across said interatrial septum by gripping against opposing sides of said interatrial septum around said implant body.

According to some embodiments of the invention, the flexible gripping skirt has a preformed bellows-like structure with foldable units, including a proximal foldable unit and a distal foldable unit, connected one with the other directly or with a non-foldable spacing unit therebetween for spacing sized to compensate for width of said interatrial septum, wherein, when said gripping sleeve is in said gripping form, said proximal foldable unit forms a proximal wing extending outwardly-radially relative to said implant body, so as to form a first proximal surface and a second proximal surface interconnected with a proximal edge, and said distal foldable unit forms a distal wing extending outwardly-radially relative to said implant body, so as to form a first distal surface and a second distal surface interconnected with a distal edge.

According to some embodiments of the invention, the gripping sleeve is in said gripping form, said first proximal surface and said second proximal surface are formed as nested conic structures extending proximally away from said proximal edge, or formed as parallel flat structures, separated by said proximal edge; or/and said first distal surface and said second distal surface are formed as nested conic structures extending distally away from said distal edge, or formed as parallel flat structures, separated by said distal edge.

According to some embodiments of the invention, the inner connector is connectable to said inner connectee by means of a screw arrangement.

According to some embodiments of the invention, the outer connector is rotationally fixable to said outer connectee while allowing relative revolving thereof around said inner connector, thereby facilitating screwing or unscrewing said inner connector and said inner connectee when connected to said outer connectee, selectively operable by at least one said handle controls.

According to some embodiments of the invention, the outer connector is connectable to said outer connectee by means of a grasper arrangement.

According to some embodiments of the invention, the grasper arrangement includes grasping jaws configured for locking onto said outer connectee having a mating recess pattern distributed circumferentially at said tubular skirt proximal end, when in a closed form.

According to some embodiments of the invention, the grasping jaws are configured in a normally closed form in absence of an opening force greater than a predetermined value.

According to some embodiments of the invention, the outer connector is connected to said outer connectee and said inner connector is disconnected with said inner connectee, said grasping jaws are shiftable from said normally closed form to an opened form by pressing said inner member against a lever mechanism in said outer connector arranged to thereby force said grasping jaws to retract outwardly.

According to some embodiments of the invention, the grasping jaws include elastically bendable arms angularly extending from said outer member to form said lever mechanism, and said inner member includes a widening sized for forcing said arms to elastically bend from a first angle indicative of said closed form to a second angle indicative of said opened form.

According to some embodiments of the invention, the widening is located at a proximal portion of said inner connector or proximally adjacent to said inner connector.

According to some embodiments of the invention, the widening is spheroidal with a narrowed portion thereof substantially mating to a collapsed concavity formable by said arms when said grasping jaws are in said closed form, and a widened portion thereof substantially mating to an enlarged concavity elastically formable by said arms when said grasping jaws are in said opened form.

According to some embodiments of the invention, the implant deployment device is provided with means to select an operative portion of said tubular skirt and to restrict said deployment device body and said handle controls to manipulate only said operative portion.

According to some embodiments of the invention, the deployment device body is dimensioned to allow lengthwise sliding of an outer sheath thereon from a distal-most implant covering position, in which said outer sheath restricts expansion or/and compression of distal portion of said tubular skirt, through an intermediate implant covering position, in which said outer sheath restricts expansion or/and compression of proximal portion of said tubular skirt and allows expansion or/and compression of said distal portion of said tubular skirt, to a fully retracted position in which the implant is fully uncovered by said outer sheath.

According to some embodiments of the invention, at least one of said handle controls is configured to selectively set travel margins of said outer sheath along said deployment device body in accordance with either of said distal-most implant covering position, said intermediate implant covering position and said fully retracted position, of said outer sheath.

According to some embodiments of the invention, at least one of said handle controls is configured to selectively operate an extendable spacer for restricting minimal distance between fixed positions, said fixed positions include: a first minimal distance by which said outer sheath is retractable up to said distal-most implant covering position, a second minimal distance by which said outer sheath is retractable up to said intermediate implant covering position, and a third minimal distance by which said outer sheath is retractable up to said fully retracted position.

According to some embodiments of the invention, the handle controls include at least one safety mechanism configured to selectively restrict at least one of: said detaching of said inner connector or/and of said outer connector when said tubular skirt is not fully compressed, or/and said detaching of said outer connector when said inner connector is connected to said inner connectee, or/and compression of proximal portion of said tubular skirt when a proximal portion of said tubular skirt is less than fully compressed.

According to some embodiments of the invention, the controls include a first knob coupled with a cam mechanism configured for effecting relative distance between the inner connector and the outer connector. According to some embodiments of the invention, the cam mechanism includes a first and a second rotatable drums, each differently affecting one of the inner connector and outer connector, wherein the first knob is selectively engageable between the first and second drums using a safety switch. According to some embodiments of the invention, the controls include a second knob configured for effecting detachment of the implant deployment device from the implant. According to some embodiments of the invention, the implant deployment device is configured such that, by continuously revolving the second knob, the inner connector and the outer connector sequentially disconnect from the inner connectee and the outer connectee, respectively.

According to an aspect of some embodiments of the present invention, there is provided a method for fixating crosswise an elongated implant to an organ wall in a subject's body, the method comprising: providing the implant attached to an implant deployment device, the implant comprising a rigid implant body enclosed with a compressible tubular skirt maintained stretched to an extended narrow form along said implant body; forming a wall opening in the organ wall; passing the implant through said wall opening until a chosen distal portion of said tubular skirt extends in front of the organ wall and a proximal portion of said tubular skirt remains behind the organ wall; while maintaining said tubular skirt proximal portion confined to said extended narrow form, compressing said tubular skirt distal portion to a first expanded form by at least partly regaining a first preformed shape of said tubular skirt distal portion while at least partly conforming to outer boundaries of said implant body and of the organ wall, and to stresses imposed by said tubular skirt proximal portion; while maintaining said tubular skirt distal portion substantially in said first expanded form, compressing said tubular skirt proximal portion to a second expanded form by at least partly regaining a second preformed shape of said tubular skirt proximal portion while at least partly conforming to outer boundaries of the organ wall; and detaching said implant from said implant deployment device.

According to some embodiments of the invention, the tubular skirt comprises a flexible gripping sleeve fixedly connected with distal end thereof to a distal periphery of said implant body and slidably connected with a proximal end thereof to said implant body along a path extending proximally to said distal periphery, wherein said method further comprises: gripping against opposing ends of the organ wall around said implant body, with said tubular skirt distal portion compressed to said first expanded form and said tubular skirt proximal portion compressed to said second expanded form, with sufficient force to maintain said implant body aligned across the organ wall.

According to some embodiments of the invention, the flexible gripping skirt has a preformed bellows-like structure with foldable units, including a proximal foldable unit comprising said tubular skirt proximal portion and a distal foldable unit comprising said tubular skirt distal portion, connected one with the other directly or with a non-foldable spacing unit therebetween for spacing sized to compensate for width of said interatrial septum, wherein said gripping against opposing ends of the organ wall includes: forcing said proximal foldable unit into forming a proximal wing extending outwardly-radially relative to said implant body, so as to form a first proximal surface and a second proximal surface interconnected with a proximal edge, and forcing said distal foldable unit into forming a distal wing extending outwardly-radially relative to said implant body, so as to form a first distal surface and a second distal surface interconnected with a distal edge.

According to some embodiments of the invention, compressing said tubular skirt proximal portion includes: pulling said implant body to so as to press said tubular skirt distal portion in said first expanded form against said organ wall until reaching a chosen shaping of said tubular skirt distal portion or/and a chosen resistance magnitude developable by said organ wall in response to said pulling.

According to some embodiments of the invention, providing the implant includes constricting said tubular skirt in said extended narrow form with constricting means.

According to some embodiments of the invention, passing the implant is first facilitated with an outer sheath sized to allow the implant passing thereinside and to maintain said tubular skirt constricted to said extended narrow form, wherein said outer sheath is progressed through said wall opening with said implant stationed therein or followed by positioning the implant therein with said tubular skirt distal portion extending in front of the organ wall.

According to some embodiments of the invention, compressing said tubular skirt distal portion to said first expanded form is first facilitated by protruding the implant out of said outer sheath such that said tubular skirt distal portion is unconstricted by said outer sheath and said tubular skirt proximal portion remains constricted by said outer sheath. According to some embodiments of the invention, compressing said tubular skirt proximal portion to said second expanded form is first facilitated by further protruding the implant out of said outer sheath such that both said tubular skirt distal portion and said tubular skirt proximal portion are unconstricted by said outer sheath.

According to some embodiments of the invention, the implant deployment device comprises a deployment device body comprising an inner member with an inner connector and an outer member with an outer connector, and wherein said providing the implant includes detachably connecting said inner connector to an inner connectee provided at a proximal end of said implant body and detachably connecting said outer connector to an outer connectee provided at a proximal end of said tubular skirt.

According to some embodiments of the invention, stretching said tubular skirt to said extended narrow form is facilitated by relatively positioning said outer connector or/and said inner connector at a first connecting distance therebetween.

According to some embodiments of the invention, compressing said tubular skirt distal portion to said first expanded form is facilitated by relatively positioning said outer connector or/and said inner connector at a second connecting distance therebetween. According to some embodiments of the invention, compressing said tubular skirt proximal portion to said second expanded form is facilitated by relatively positioning said outer connector or/and said inner connector at a third connecting distance therebetween.

According to some embodiments of the invention, shifting from said second connecting distance to said third connecting distance is effected only upon releasing a first safety.

According to some embodiments of the invention, the first safety is releasable only when said outer connector is positioned at said second connecting distance relative to said inner connector.

According to some embodiments of the invention, detaching said implant from said implant deployment device includes separately and sequentially disconnecting said inner connector from said inner connectee and said outer connector from said outer connectee. According to some embodiments of the invention, disconnecting said inner connector is followed by disconnecting said outer connector. According to some embodiments of the invention, the inner connector is connectable to said inner connectee by means of a screw arrangement and said disconnecting said inner connector includes: holding said outer connectee rotationally fixed with said outer connector; and revolving, via clockwise or counterclockwise directional motion, said inner connector relative to said inner connectee until unscrewing said inner connector. According to some embodiments of the invention, the outer connector is connectable to said outer connectee by means of a grasper arrangement, said grasper arrangement comprising grasping jaws configured for locking onto said outer connectee having a mating recess pattern, and said disconnecting said outer connector includes: after disconnecting said inner connector, pressing said inner member against a lever mechanism in said outer connector so as to force said grasping jaws to retract outwardly.

According to an aspect of some embodiments of the present invention, there is provided a method for sealing a wall opening in a septal wall in a subject's body, the method comprising: providing an implant attached to an implant deployment device, said implant comprising a rigid implant body enclosed with a compressible tubular skirt maintained stretched to an extended narrow form along said implant body, wherein said tubular skirt comprises a flexible gripping sleeve fixedly connected with distal end thereof to a distal periphery of said implant body and slidably connected with a proximal end thereof to said implant body along a path extending proximally to said distal periphery; passing said implant through the wall opening until a chosen distal portion of said tubular skirt extends in front of the septal wall and a proximal portion of said tubular skirt remains behind the septal wall; while maintaining said tubular skirt proximal portion confined to said extended narrow form, compressing said tubular skirt distal portion to a first expanded form by at least partly regaining a first preformed shape of said tubular skirt distal portion while at least partly conforming to outer boundaries of said implant body and of the septal wall, and to stresses imposed by said tubular skirt proximal portion; while maintaining said tubular skirt distal portion substantially in said first expanded form, compressing said tubular skirt proximal portion to a second expanded form by at least partly regaining a second preformed shape of said tubular skirt proximal portion while at least partly conforming to outer boundaries of the septal wall; and detaching said implant from said implant deployment device.

According to some embodiments of the invention, the method further comprises: gripping against opposing ends of the septal wall around said implant body, with said tubular skirt distal portion compressed to said first expanded form and said tubular skirt proximal portion compressed to said second expanded form, with sufficient force to maintain said implant body aligned across the septal wall.

According to some embodiments of the invention, the flexible gripping skirt has a preformed bellows-like structure with foldable units, including a proximal foldable unit comprising said tubular skirt proximal portion and a distal foldable unit comprising said tubular skirt distal portion, connected one with the other directly or with a non-foldable spacing unit therebetween for spacing sized to compensate for width of said interatrial septum, and wherein said gripping against opposing ends of the septal wall includes: forcing said proximal foldable unit into forming a proximal wing extending outwardly-radially relative to said implant body, so as to form a first proximal surface and a second proximal surface interconnected with a proximal edge, and forcing said distal foldable unit into forming a distal wing extending outwardly-radially relative to said implant body, so as to form a first distal surface and a second distal surface interconnected with a distal edge.

According to some embodiments of the invention, compressing said tubular skirt proximal portion includes: pulling said implant body to so as to press said tubular skirt distal portion in said first expanded form against said septal wall until reaching a chosen shaping of said tubular skirt distal portion or/and a chosen resistance magnitude developable by said septal wall in response to said pulling.

According to some embodiments of the invention, providing said implant includes constricting said tubular skirt in said extended narrow form with constricting means.

According to some embodiments of the invention, passing said implant is first facilitated with an outer sheath sized to allow said implant passing thereinside and to maintain said tubular skirt constricted to said extended narrow form, wherein said outer sheath is progressed through said wall opening with said implant stationed therein or followed by positioning said implant therein with said tubular skirt distal portion extending in front of the septal wall.

According to some embodiments of the invention, compressing said tubular skirt distal portion to said first expanded form is first facilitated by protruding said implant out of said outer sheath such that said tubular skirt distal portion is unconstricted by said outer sheath and said tubular skirt proximal portion remains constricted by said outer sheath. According to some embodiments of the invention, compressing said tubular skirt proximal portion to said second expanded form is first facilitated by further protruding said implant out of said outer sheath such that both said tubular skirt distal portion and said tubular skirt proximal portion are unconstricted by said outer sheath.

According to some embodiments of the invention, the implant deployment device comprises a deployment device body comprising an inner member with an inner connector and an outer member with an outer connector, and wherein said providing said implant includes detachably connecting said inner connector to an inner connectee provided at a proximal end of said implant body and detachably connecting said outer connector to an outer connectee provided at a proximal end of said tubular skirt.

According to some embodiments of the invention, stretching said tubular skirt to said extended narrow form is facilitated by relatively positioning said outer connector or/and said inner connector at a first connecting distance therebetween. According to some embodiments of the invention, compressing said tubular skirt distal portion to said first expanded form is facilitated by relatively positioning said outer connector or/and said inner connector at a second connecting distance therebetween. According to some embodiments of the invention, the compressing said tubular skirt proximal portion to said second expanded form is facilitated by relatively positioning said outer connector or/and said inner connector at a third connecting distance therebetween.

According to some embodiments of the invention, shifting from said second connecting distance to said third connecting distance is effected only upon releasing a first safety. According to some embodiments of the invention, the first safety is releasable only when said outer connector is positioned at said second connecting distance relative to said inner connector.

According to some embodiments of the invention, detaching said implant from said implant deployment device includes separately and sequentially disconnecting said inner connector from said inner connectee and said outer connector from said outer connectee. According to some embodiments of the invention, disconnecting said inner connector is followed by disconnecting said outer connector. According to some embodiments of the invention, the inner connector is connectable to said inner connectee by means of a screw arrangement and said disconnecting said inner connector includes: holding said outer connectee rotationally fixed with said outer connector; and revolving, via clockwise or counterclockwise directional motion, said inner connector relative to said inner connectee until unscrewing said inner connector. According to some embodiments of the invention, the outer connector is connectable to said outer connectee by means of a grasper arrangement, said grasper arrangement comprises grasping jaws configured for locking onto said outer connectee having a mating recess pattern, and said disconnecting said outer connector includes: after disconnecting said inner connector, pressing said inner member against a lever mechanism in said outer connector so as to force said grasping jaws to retract outwardly.

According to some embodiments of the invention, the rigid implant body has a total length between 5 mm and 50 mm, optionally between 10 mm and 30 mm, optionally between 15 mm and 20 mm, optionally about 18 mm, and has a maximal outer diameter being about 5 mm or less, optionally about 3.5 mm or less, or optionally about 2 mm or less.

According to some embodiments of the invention, the tubular skirt in its extended and narrowed form is about 25 mm to about 100 mm in length, optionally about 50 mm in length, and is sized for unhindered passage when constricted to a diameter of 2 to 4 mm, such as through a 12 French outer sheath/catheter (i.e., about 4 mm outer diameter) or/and is about 6 mm or less in diameter if not constricted. The septum opening is optionally substantially smaller than the outer sheath outer diameter but is elastically stretched wide when passing therethrough, optionally about 1 mm to about 3 mm (slit or puncture), optionally using formed using a 5 to 8 French (1.25 mm to 2.67 mm) trans-septal puncture kit. Tubular skirt may be loaded into the outer sheath via a gradually constricting passage, such as from about 7-10 mm down to 3.8-4.2 mm in diameter.

When in the (radially expanded) gripping form, the tubular skirt may be less than about 25 mm, optionally about 15 mm or less in length, and about 10 mm or more, optionally about 15 mm or about 18 mm or more, in diameter. The tubular skirt may be formed of a mesh having intertwined members (e.g., fibers, cords or the like), optionally made of metal (e.g., Ni—Ti alloy). In one exemplary embodiment the mesh includes 42 intertwined (one over one) Ni—Ti 100 micron fibers/cords Fiber diameter, optionally with light oxide surface finish, and 90-degree intersection angle.

In an aspect of some embodiments there is provided a wireless pressure sensor implant, provided in a miniature packaging, with a dedicated delivery system. According to some embodiments of the invention, the implant is a part of a sensory system (also comprising a remote device applicable from outside subject's body configured for monitoring physiological data from within the human body, for example direct pressure measurement from within the heart's left atrium.

According to some embodiments of the invention, the implant includes anchoring means designed for fixating on to a wall of an internal body organ, for example the inter-atrial septal wall, implantable via a minimal invasive procedure.

According to some embodiments of the invention, the implant includes sensing elements are integrated into a tube shaped (rigid) implant body which contains the electronic circuitry.

According to some embodiments of the invention, the implant includes several subassemblies, for example: (i) a sensory element cup assembly that includes electrical feedthrough, which can house for example a pressure sensing traducers positionable on one or both ends of the implant, (ii) a brazed tube assembly comprising a tube applied with a braided (mesh) fixation means, and (iii) an inner electronic assembly that includes electronic circuitry for interfacing with the sensing element and communicating the data to the external unit.

According to some embodiments of the invention, the inner electronic assembly may include one or more of the followings: (i) a dedicated application-specific integrated circuit (ASIC) that is mounted on a miniature printed circuit board (PCB) that is applied with other discreet elements, (ii) an RF antenna, which is electrically connected to the PCB and includes a metallic core wrapped with a conductive coil.

The implant body (tube) may be 1 mm, 2 mm, 2.5 mm, 3.5 mm or up to 5 mm in outer diameter, and 8 mm, 10 mm, or up to 22 mm in length. The fixation means (e.g., a septum gripper, optionally including a mesh or a braided pattern) may be 10 to 24 mm wide/diameter, when fully deployed (radially expanded). These fixation means, when crimped (e.g., stretched or/and narrowed) are optionally deliverable through lumen of an 8-French (Fr), 10-Fr, 11-Fr, 12-Fr, or a larger diameter, or a smaller diameter, sheath.

According to some embodiments of the invention, the implant body is made of a metal with possible combination of ceramic. The implant body is optionally configured particularly to endure internal body environment providing biocompatibility and structural strength, and to allow sufficient Radio Frequency (RF) communication between the implant and its external unit for transmitting power and digital information, to process and transmit physiological information from the sensor. Optionally, implant body segment which houses the antenna may be an RF compatible tube, and may be either non-metallic/electrical non-conductive (optionally made from zirconia or titania) or metallic with grooves. An example for non-metallic tube it is ceramic.

According to some embodiments of the invention, the implant fixation means (septum gripper) is made of either a metallic and/or polymeric material or with any other material combination that is either electrical conductive or electrical non-conductive in nature. Optionally, the fixation means include a mesh (e.g., braid) made from Ni—Ti alloy ('Nitinol') which is thermally shaped to preformed double-sided wall gripping form shape, and is configured for mechanical stabilization in human body temperature, yet deformable for allowing forming from a crimped (narrowed or/and stretched) from to its expanded form.

According to some embodiments of the invention, the implant fixation means (septum gripper) is connected to the rigid implant body using several designated fixtures. Optionally, at least one of the fixtures includes inner and outer rings configuration, sandwiching a portion of the septum gripper (sleeve/mesh) therebetween. Fixtures may optionally be made from electrically non-conductive materials for isolating the septum gripper (sleeve) from electrically conductive parts of the implant body, as well as for sealing and mechanically protecting outer edges of the sleeve (mesh/braid). Two fixtures may exist for both the proximal end and the distal braid end.

According to some embodiments of the invention, the implant is deliverable, deployable or/and fixatable using a delivery kit or system which may include a trans-septal outer sheath and dilator kit, an implant loader (into outer sheath), and an implant delivery/deployment device which may include a rod-like element or a cable connectable to the implant and applicable for pushing the implant through the outer sheath until reaching the target deployment location, and be released after the implant has been positioned properly. Prior to implantation with the dedicated delivery system the septal wall may be punctured using any standard trans-septal puncturing kit and in accordance to known practice.

According to some embodiments of the invention, the implant is positioned across the interatrial septum. Optionally, implantation is carried out following standard trans-septal puncture and passage typically using a femoral venous approach. Following sheath and wire positioning in the left atrium or alternatively in a pulmonary vein, the implant may be introduced through the sheath to a chosen position or/and orientation in the left atrium. The implant is optionally inserted either preloaded within a dedicated catheter or pushed directly through the outer sheath prior to deployment and fixation across the interatrial septum.

According to some embodiments of the invention, the implant is first introduced partially within the left atrium followed by deployment (expansion) of gripping sleeve distal end only, and it is slowly and safely exposed within the left atrium by gradual retraction of the outer sheath. The septum gripper is shaped and configured for recollapsing into the outer sheath and allows for adjustment of the space between its gripping surfaces in conformity to wall anatomy (such as the interatrial septum thickness. Deployment of the proximal part of the septum gripper is optionally performed after fully exposing the septum gripper from the outer sheath, optionally under vision using fluoroscopy or/and echocardiography. Following confirmation of device position across the interatrial septum and its stability, the implant can be detached from the implant deployment device. Complete retrieval of the implant is possible during the deployment at least until complete detachment of the deployment device from the implant.

According to some embodiments of the invention, the deployment procedure may include at least one of the following steps (not necessarily in same order):

holding the outer sheath in place and slowly advance the implant forward using the implant deployment device until the implant is aligned with the distal tip of the outer sheath.

under echocardiographic guidance or/and fluoroscopy, repositioning the outer sheath so that its distal tip is approximately 2-3 cm distal to the Fossa Ovalis inside the left atrium.

retract the outer sheath while keeping the implant in-place using the implant deployment device, until a chosen distal portion of the septum gripper (gripping sleeve) is exposed in the left atrium and radially expands.

verifying that the expanded distal portion of the sleeve opposes correctly the interatrial septum.

further retracting the outer sheath until exposing the rest of the septum gripper.

expanding the proximal side of the septum gripper.

following confirmation of stability, disengage the implant deployment device from the implant.

removing the outer sheath and the implant deployment device.

All technical or/and scientific words, terms, or/and phrases, used herein have the same or similar meaning as commonly understood by one of ordinary skill in the art to which the invention pertains, unless otherwise specifically defined or stated herein. Exemplary embodiments of methods (steps, procedures), apparatuses (devices, systems, components thereof), equipment, and materials, illustratively described herein are exemplary and illustrative only and are not intended to be necessarily limiting. Although methods, apparatuses, equipment, and materials, equivalent or similar to those described herein can be used in practicing or/and testing embodiments of the invention, exemplary methods, apparatuses, equipment, and materials, are illustratively described below. In case of conflict, the patent specification, including definitions, will control.

Implementation of some embodiments of the invention, for example, at least those embodiments of, or including use of, the implant deployment device for delivering and deploying an implant, where the implant deployment device includes 'a handle having controls (controllers)', can involve performing or completing selected tasks manually, automatically, or a combination thereof. Controls may include for example any element that can be applied manually or otherwise for triggering a chosen preset event, and these may include a button, a knob, a switch, a trigger, voice recognition, gesture recognition, or any other type of this sort. Moreover, according to actual instrumentation and equipment of some embodiments of the invention, several selected tasks could be implemented by hardware, by software, by firmware, or a combination thereof, using an operating system.

For example, hardware for performing selected tasks according to embodiments of the invention could be implemented as a chip, as a circuit, or a combination thereof. As software, selected tasks of some embodiments of the invention could be implemented as a plurality of software instructions being executed by a computer using any suitable operating system. In an exemplary embodiment of the invention, one or more tasks of exemplary embodiments of the method or/and system as described herein are performed by a data processor, such as a computing platform for executing a plurality of instructions. Optionally, the data processor includes a volatile memory for storing instructions or/and data. Alternatively or additionally, optionally, the data processor includes a non-volatile storage, for example, a magnetic hard-disk or/and removable media, for storing instructions or/and data. Optionally, a network connection is provided as well. Optionally, a display or/and a user input device such as a keyboard or mouse is provided as well.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 5A-5B are schematic side cut views of a defected organ wall before and after deploying an exemplary implant, in accordance with some embodiments of the present invention;

FIGS. 6A-6B are schematic side cut views of a body organ with an organ wall before and after deploying an exemplary sensory implant, in accordance with some embodiments of the present invention;

FIGS. 8A-8G are schematic side or isometric views of an exemplary implant deployment device configured for implantation and deployment of the implant of the invention, in accordance with some embodiments of the invention;

DESCRIPTION OF SPECIFIC EMBODIMENTS OF THE INVENTION

Figure 1A:
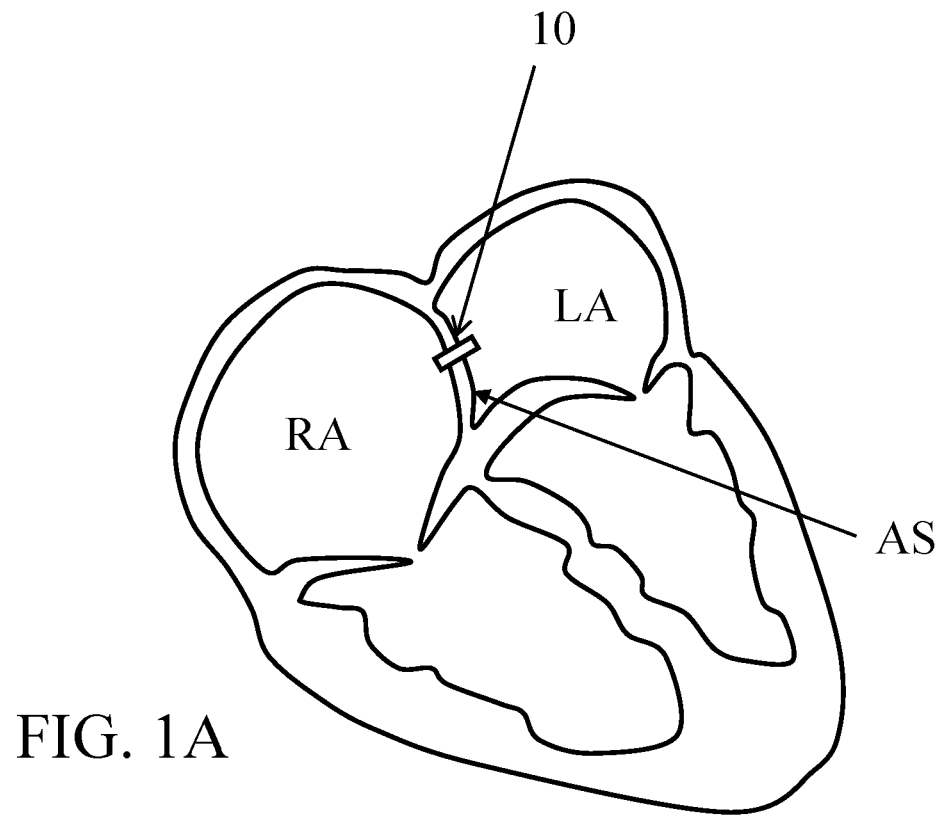
FIGS. 1A-1B are a schematic views of a human heart (FIG. 1A), showing an exemplary implant configured for implantation in the atrial septum (AS) and to extend from the right atria (RA) to the left atria (LA), and communication capabilities between the implant and an external unit (FIG. 1B), in accordance with some embodiments of the invention.

The present invention relates to an implant deployment device, and method using thereof, for deploying and fixating an implant across an organ wall in a subject. Also disclosed are exemplary embodiments of a method for sealing a wall opening in a septal wall in a subject's body.

There is a requirement to provide wall mounting/fixating means for implants, particularly implants which are deliverable (e.g., transcatheter delivery) into a body organ that is separated by an organ wall, where the implant is to reside across this organ wall. Usually such an implant is provided across a naturally occurring opening (e.g., a normal opening or an abnormal/defect opening) or a premade opening (e.g., hole, cut, or puncture) and is fixated by pressing against the two sides of the organ wall around the wall opening. There is still an unmet for such fixating/mounting means due to the combination of the following requirements:

such means should be stored and delivered in a very small diameter constrictive channels, for example diameters of 4 mm or even 3 mm and less, without deteriorating their structure and function when expanded for fixating the implant to the organ wall.

such means should be able to inherently compensate for different dimensions of the wall, for example wall thickness which may be substantially variable, without compensating for their structure and function when expanded for fixating the implant to the organ wall.

such means should be able to deform into final fixation (e.g., gripping) form without relying on anatomy, as in current practice the deployment of transseptal implants (e.g., septal occluders) is done by extracting the implant (thereby allowing its fixation means to self-expand) out of an outer sheath against the organ wall margins surrounding the wall opening, yet the opening size may not allow that practically or efficiently.

such means should be able to recollapse and retrieve for optional discarding or redeployment (e.g., in a different target location), since that, especially with respect to sensory implants, implant's functionality can be determined only after deployment.

Exemplary embodiments of the present invention relate to an implant capable of being deployed and positioned within the heart, particularly, in the atrial septum. Such an implant is further configured and useful for sensing or/and measuring, and optionally, monitoring, one or more physiological conditions or/and parameters in a chamber of a heart of a patient. In exemplary embodiments, the implant may include a wireless pressure sensor being miniature in size. Exemplary embodiments of the present invention are suitable for being in the form of a system or/and a kit, including an implant having an implant body with sensing or/and measuring means and a septum gripper, a minimal invasive delivery/deployment system, and a (electronic) unit for externally, interactively communicating with the implant sensing or/and measuring means.

The implant in exemplary embodiments of the invention facilitates sensing or/and measuring a physiological condition or/and parameter, such as pressure within at least one of the left and right atrium, optionally, particularly in the left atrium. Such sensing or/and measuring are of particular importance especially when associated with heart failure patients (e.g., CHF patients). In such modalities, continuous heart pressure monitoring may be effective for assessing and managing disease progression. Timely interventions including medication taken as immediately as possible after an increase in pressure may be considered more effective for applying timely treatment to a CHF patient or/and for reducing unnecessary hospitalization.

The implant in exemplary embodiments of the invention may provide a long felt need in providing heart pressure monitoring for long periods (e.g., about 5 years or more, optionally about 10 years or more).

Referring now to the drawings, FIG. 1A is a schematic frontal cut view of a human heart showing the atrial septum (AS). Atrial septum is the wall that separates the right atrium (RA) from the left atrium (LA) of the heart. This term is interchangeable with the term "interatrial septum". As shown in FIG. 1A and will be explained in more details below, the implant of the invention, is configured to be placed through or reside within the atrial septum. In FIG. 1A, a simplified illustration of implant 10, in accordance with some embodiments of the invention is shown.

The implant may include sensing or/and measuring means. The term "sensing or/and measuring means", as used herein, refers to component(s) or/and electronics that enable and facilitate sensing or/and measuring and transmitting data associated with one or more physiological conditions or/and parameters of the heart/cardiac system that may be processed to provide information regarding condition of a patient's heart. According to some embodiments, the mean(s) include at least a pressure sensor or transducer capable of specifically sensing or/and measuring, or measurably reacting to, pressure (or change thereof, or difference thereof with ambient pressure, for example) within the heart (e.g., particularly in the left atrium).

Figure 1B:
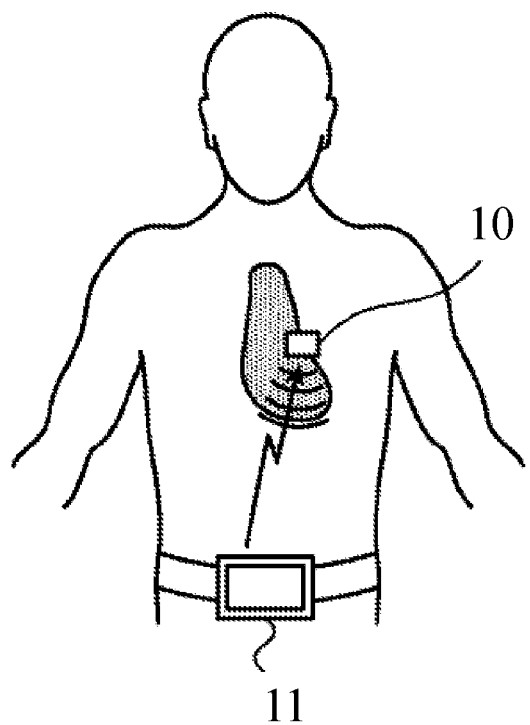

The term "sensing or/and measuring means", as used herein, is interchangeable with the term "operational member" or may be considered a component or a part thereof. The data transmitted from the sensing or/and measuring means may include, without limitation, at least one of the following physiological conditions or/and parameters: pressure, stress, heart rate, anatomical abnormalities (e.g., valve malfunction), temperature, blood flow rate, and gas (e.g., oxygen) concentration or/and volume. The data transmitted from the sensing or/and measuring means is transmitted wirelessly to an external unit 11 located outside patient's body (As shown in FIG. 1B), and configured for communicating (i.e., reading, processing and providing an input) with the sensing or/and measuring means, which includes for example reading, analyzing or/and processing a data (picked-up by the sensing or/and measuring means or/and combined with stored data or/and newly introduced data) to provide a readout by the external unit. According to some embodiments, the external unit may also provide power to the sensing or/and measuring means or/and to other components thereinside. The implant includes a (selectively deployable) septum gripper configured to grip on to the septum, such as from both sides thereof. The septum gripper includes a first and a second foldable units. In exemplary embodiments, the first and the second foldable units are configured to shift from an extended delivery form to a gripping form, such that, in the delivery form, the foldable units are extended and the implant is capable of passing through an opening of the septum, and in the gripping form, the foldable units are deployed and the septum is gripped or clamped in-between the two foldable units.

The implant further includes at least one sensing means confined within the implant body and adapted to monitor physiological parameter(s) within a heart cavity.

The description that follows illustrates possible example embodiments of the implant and its delivery and anchoring (e.g., fixating, such as by gripping). The embodiments described herein are depicted purely by way of example, and various other suitable implementations can be used in alternative embodiments.

Figure 2A:
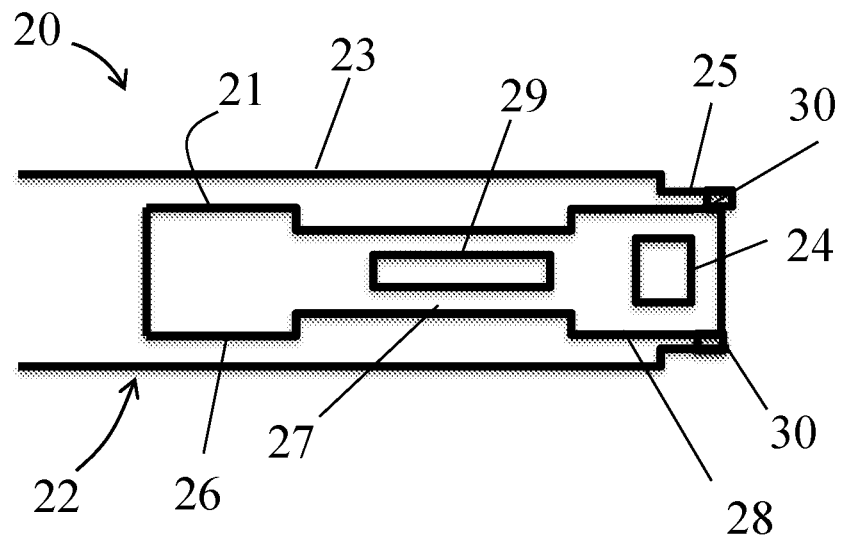
FIGS. 2A-2B are schematic side cut views of an exemplary implant, having an implant body, and a septum gripper that includes a proximal foldable unit and a distal foldable unit, the septum gripper is connected and fixated to the implant body at a sleeve fixation area located distally to the distal foldable unit, in accordance with some embodiments of the present invention.
Figure 2B:
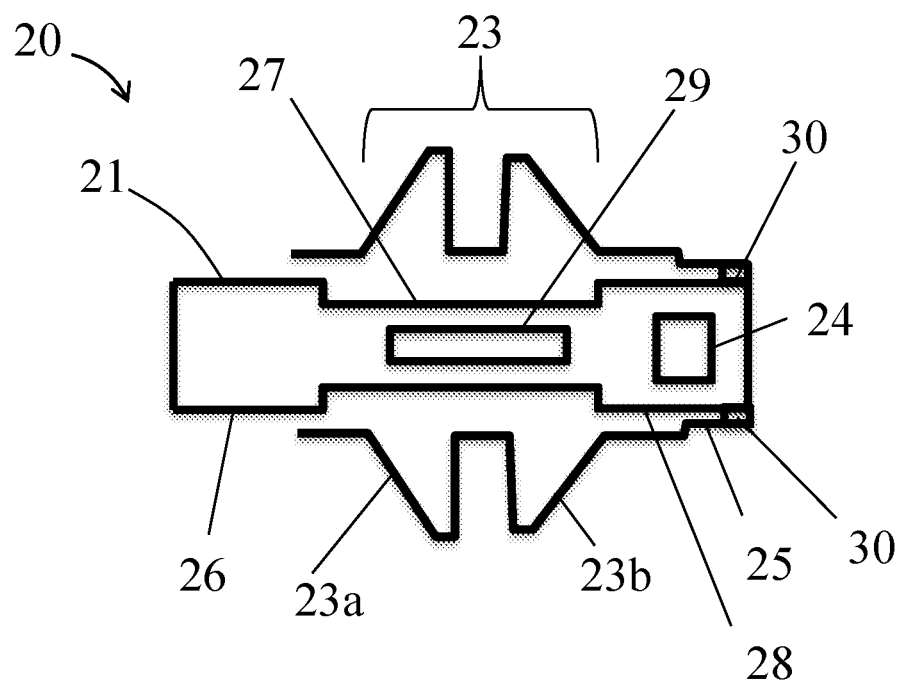

Reference is now made to FIGS. 2A-2B, which schematically illustrate side, cut views of an implant 20, in accordance with some embodiments of the invention. Implant 20 includes implant body 21 which houses sensing means 24 capable for sensing or/and monitoring, or/and detecting a condition in a chamber of the heart. Implant 20 further includes septum gripper 22 including gripping sleeve 23 shapeable from an extended delivery form (FIG. 2A) sized to pass through a septum opening in an atrial septum, to a non-bounded gripping form configured for gripping onto atrial septum (FIG. 2B). Gripping sleeve 23 includes proximal foldable unit 23a and distal foldable unit 23b (shown in FIG. 2B). Gripping sleeve 23 further includes a non-foldable sleeve portion 25 that is not changing in dimensions during sleeve change in shape when the gripping sleeve 23 transforms from an extended delivery form to a gripping form.

Implant body 21 of implant 20 includes a first elongated wall segment 26 of a first outer dimension and a second elongated wall segment 27 of a second outer dimension. Implant body 21 of implant 20 may further include a third elongated wall segment 28. According to some embodiments, the outer dimension of the second elongated wall segment 27 is smaller than the outer dimension of the first elongated wall segment 26.

According to some embodiments, first wall segment 26 and optionally, second elongated wall segment 28 is formed of metal alloy. Suitable metal alloys include, but are not limited to alloys comprising Titanium (Ti). The Alloys may have a certain purity. For example, the Ti alloy may be of grade II. According to some embodiments, the second wall segment 27 is formed from a ceramic material such as zirconia or alumina. According to some embodiments, the second wall segment 27 houses a metal coil or/and an antenna 29 configured for transmitting or/and receiving radio-frequency electromagnetic wave. According to some embodiments, gripping sleeve 23 is connected to implant body 21 only through non-foldable sleeve portion 25. According to some embodiments, non-foldable sleeve portion 25 is connected to implant body 21 through sleeve fixation area 30. According to some embodiments and as shown in the FIG. sleeve fixation area 30 may be disposed distally to the distal foldable unit 23a. The sleeve fixation area 30 may include an inner and an outer ring, wherein the outer ring clamps the inner ring which in turn clamps the distal non-foldable sleeve portion, thereby fixating distal non-foldable sleeve portion to implant body 21.

Figure 3A:
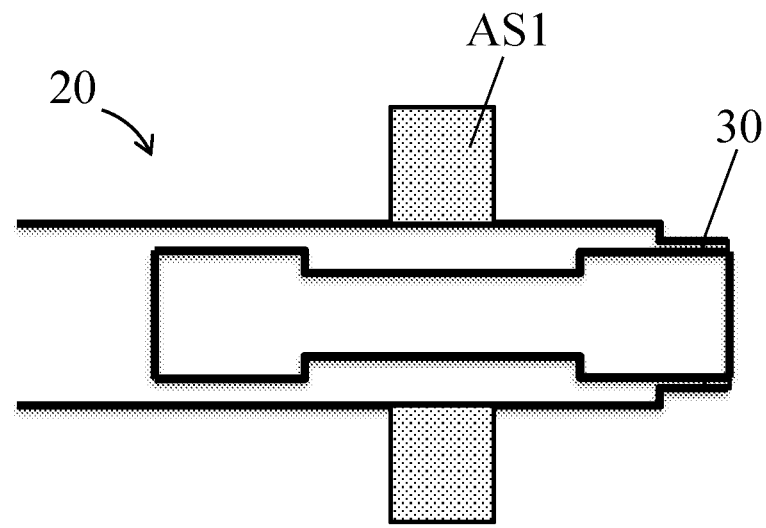
FIGS. 3A-3B are schematic side cut views of an exemplary implant, when in the delivery form (FIG. 3A) configured to cross an atrial septum AS1 having a first wall thickness, and the gripping form (FIG. 3B) that grips the atrial septum AS1 having a first wall thickness, in accordance with some embodiments of the present invention.
Figure 3B:
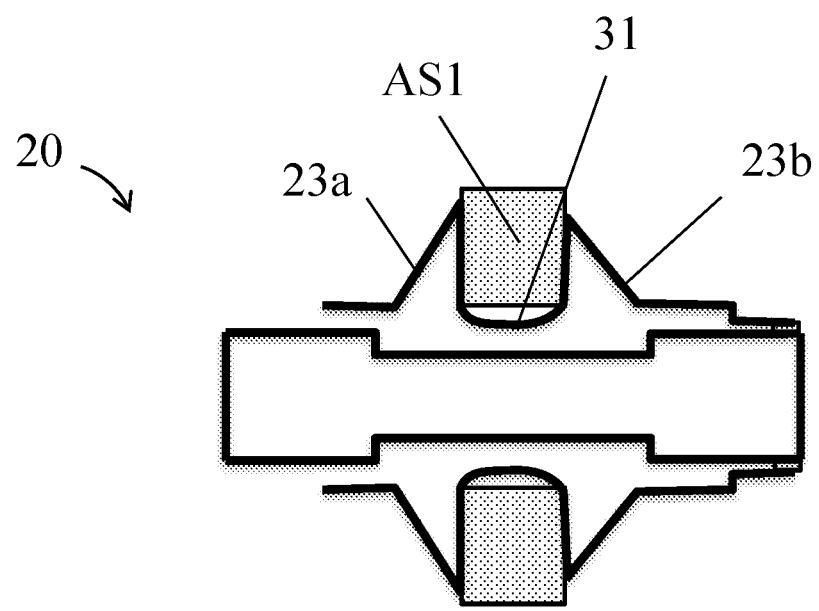

Reference is now made to FIGS. 3A-3B, which show implant 20 of the invention when extending across a premade opening in a first atrial septum AS1, when in the delivery form (FIG. 3A), and in a gripping form (FIG. 3B), where it grips the atrial septum AS1. In this example the atrial septum (wall) is relatively thin. Atrial septum wall thickness may vary substantially between patients. Typically, atrial septum wall thickness ranges between about 1 mm to about 20 mm. Implant 20 is optionally configured to accommodate various atrial septum wall thicknesses and is therefore adjustable to all atrial septum wall sizes. Specifically, at least one of: proximal foldable unit 23a, spacing unit 31, and distal foldable unit 23b are elastically stretchable and at the same time maintain septum gripping functionality.

FIGS. 4A-4L are schematic side cut views representing steps of an exemplary method of delivering, deploying and fixating an exemplary implant 40 with an exemplary implant deployment device 41. Implant may be similar to in function or/and in structure to implant 20 and possesses a rigid implant body 42 enclosed with a compressible tubular skirt 43. Implant deployment device 41 includes a deployment device body 44 that is dimensioned, structured and configured to push implant 40 in a subject's blood vessel ('BV'), such as via peripheral blood vessels, up to right atrium ('RA') of the heart, and across an interatrial septum (septal wall, 'SW'), into a left atrium ('LA') in subject's heart. The subject may be a live human or animal which may breathe or/and circulate blood on his own, or use dedicated auxiliary machines.

Deployment device body 44 includes an inner member 45 with an inner connector 46 at a distal end thereof. Inner connector 46 is adapted to detachably connect to an inner connectee 47 provided at a proximal end 48 of implant body 42. Deployment device body 44 also includes an outer member 49 with an outer connector 50 at a distal end thereof. Outer connector 50 is adapted to detachably connect to an outer connectee 51 provided at a proximal end 52 of said tubular skirt 43.

Figure 4A:
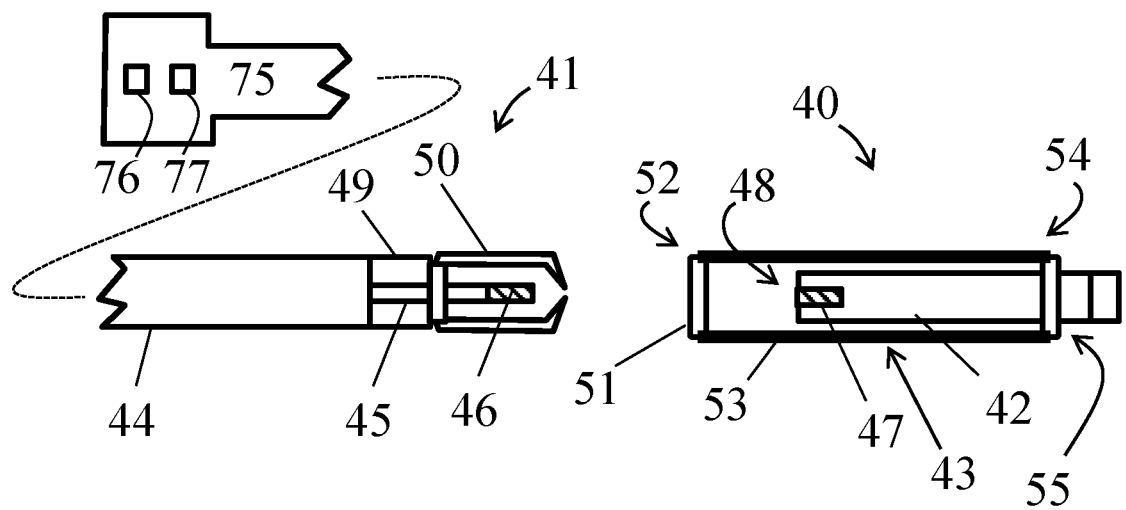
FIGS. 4A-4L are schematic side cut views representing steps of an exemplary method of delivering and deploying an exemplary implant with an exemplary implant deployment device, in accordance with some embodiments of the present invention.
Figure 4B:
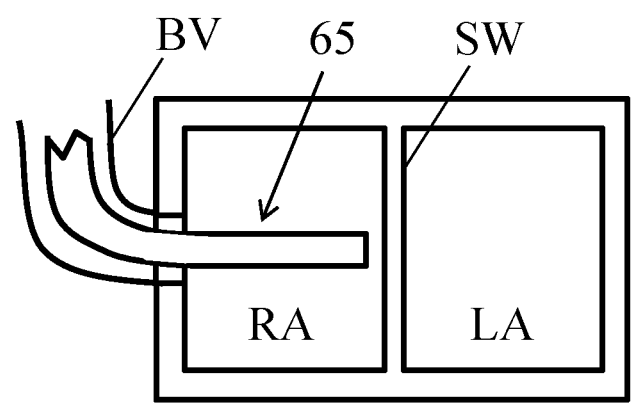

In exemplary embodiments, implant deployment device 41 includes a handle 75 (which may be similar in function or/and structure to handle 305 shown in FIGS. 10A-10E) operatively connected to proximal ends of inner member 45 and outer member 49 of deployment device body 44. In exemplary embodiments, handle 75, includes controls (controllers), for example, controls 76 and 77 (FIG. 4A), for example, in a form of knobs or/and switches (such as distal knob 308 and proximal knob 309, provided in handle 305, for example, as shown in FIG. 11 (I)) as part of the operative connection of the handle to the proximal ends of inner member 45 and outer member 49 of deployment device body 44. Controls 76 and 77 are configured and assigned to selectively operate positioning of outer connector 50 longitudinally relatively to inner connector 46 (for example, in the relative longitudinal shift therebetween shown in FIG. 4D verses to as shown in FIG. 4A). Such relative positioning can be used to facilitate: (i) determining extent of compression of tubular skirt 43 along implant body 42, (ii) to selectively operate inner connector 46 detaching from or/and connecting to inner connectee 47, and (iii) to selectively operate outer connector 50 detaching from or/and connecting to outer connectee 51. Exemplary controls (controllers) 76 and 77 of the handle 75 are knobs, switches, actuators (servomechanisms), and similar types of mechanical or/and electromechanical devices and components, configured and functioning singly, or in combination, that enable the handle to be used for operating, manipulating, and positioning the implant deployment device, for example, implant deployment device 41.

Connecting or/and detaching operation of the outer connector 50 is optionally mechanically enabled separately to connecting or/and detaching operation of inner connector 46, and this may be advantageous for reconnecting implant deployment device 41 to implant 40 following implant deployment and detachment (partial, by either one of inner and outer connectors, or full, following detachment of both). For example, connection type used to connect outer connector 50 to outer connectee 51, when inner connector 46 is not connected, may be configured to allow freedom of motion or/and flexibility in motion of implant body 42 relative to implant deployment device 41, in one or more axes, thereby allowing it to be subject to bodily motions, such as subject's heart motions. The medical practitioner, hence, under vision, can analyze and determine deployment result in view of implant stability or/and functional behavior (e.g., as a sensory/measuring implant) closer to its conditions when fully detached. In case deployment result is determined suboptimal, the medical practitioner can simply and immediately reconnect inner connector 46 to inner connectee 47 and decide, for example, if to remove and locate implant 40 in another location or only change implant orientation or/and fixation characteristics to septal wall SW.

Tubular skirt 43 includes (or is in a form of) a flexible gripping sleeve 53, which is fixedly connected with distal end thereof 54 to a distal periphery 55 of implant body 42 and slidably connected with proximal end 52 thereof to implant body 42 along a path extending proximally to distal periphery 55. Gripping sleeve 53 is compressible into a gripping form (optionally with tendency to regain a preformed shape, such as in result of casting or/and pressing over a shaped mandrel during sleeve forming), as the sleeve form shown in FIG. 4L, with sufficient force to maintain implant body 42 oriented (e.g., aligned) within left atrium LA across the interatrial septum SW, by gripping against opposing sides of the interatrial septum SW around implant body 42.

Figure 4C:
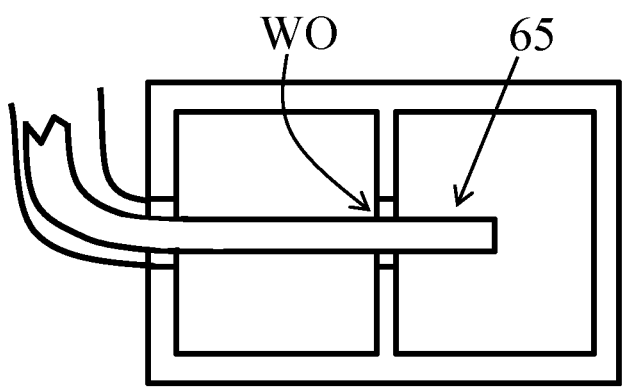
Figure 4D:
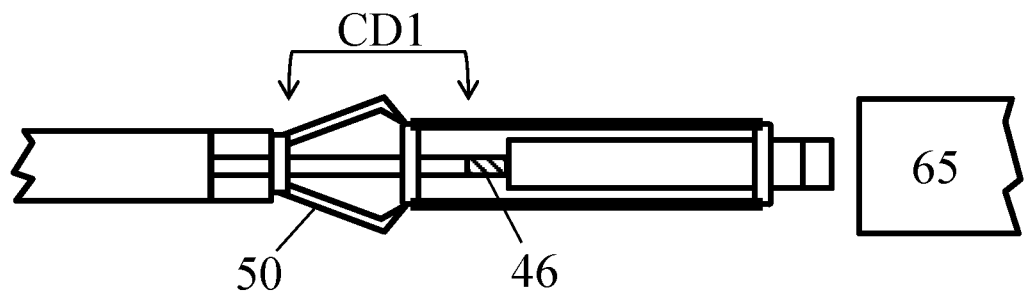
Figure 4E:
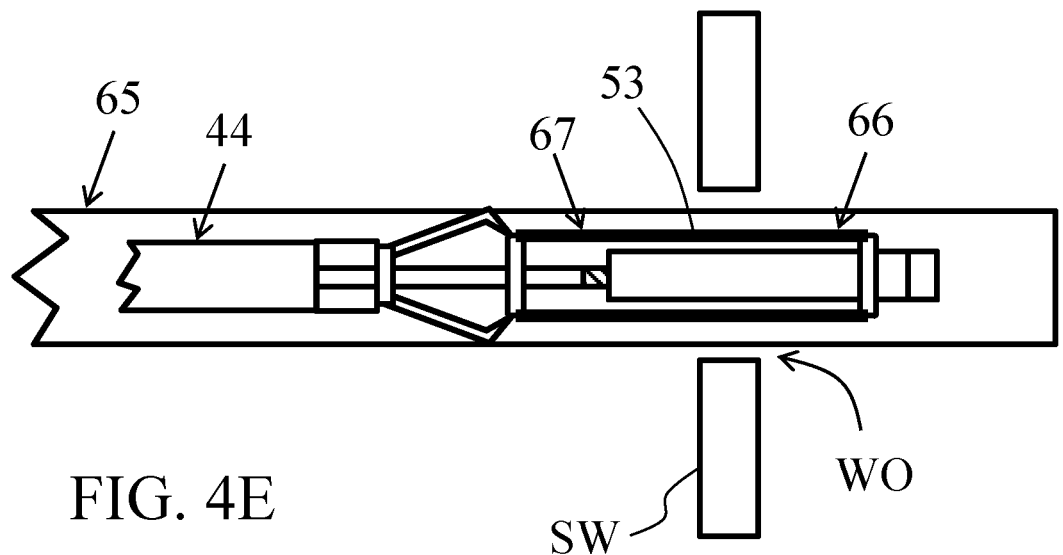
Figure 4F:
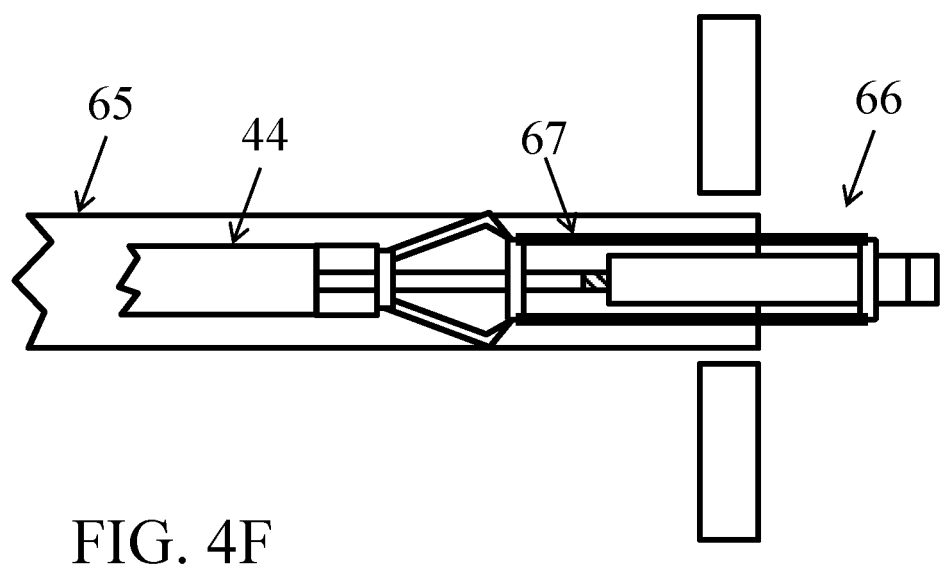
Figure 4G:
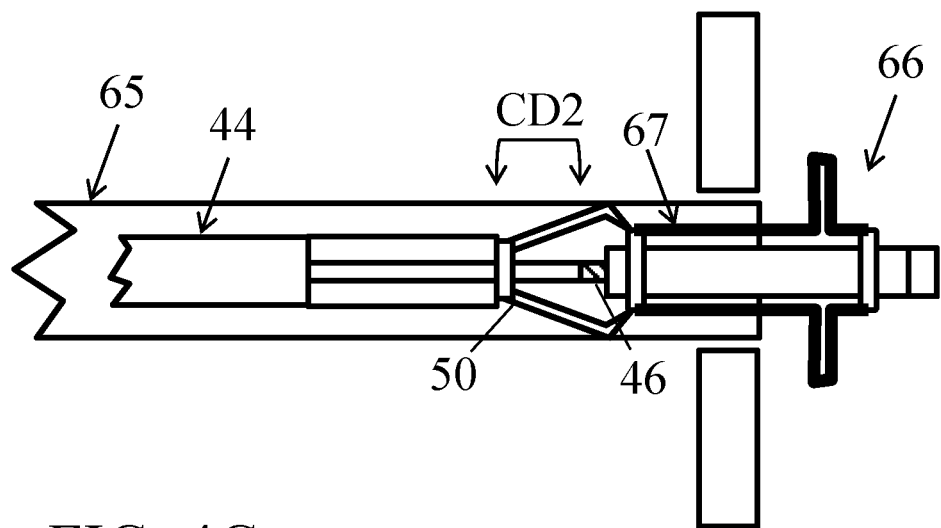
Figure 4H:
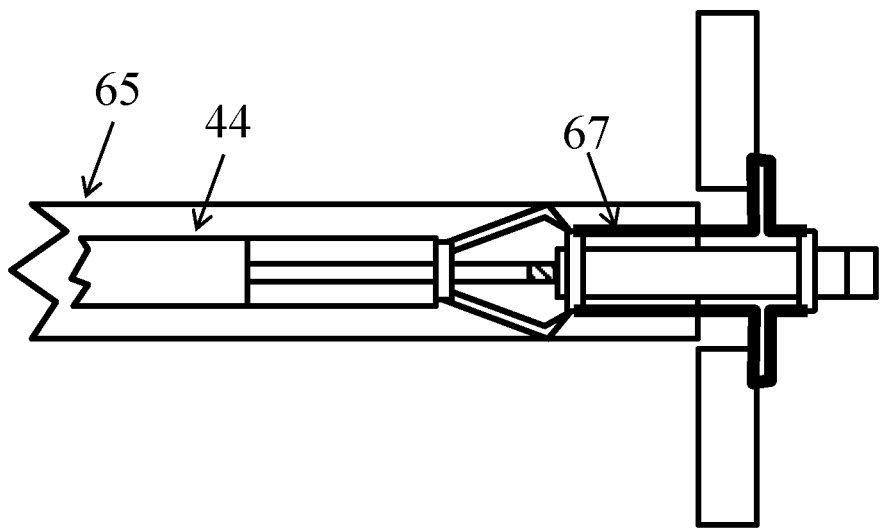
Figure 4I:
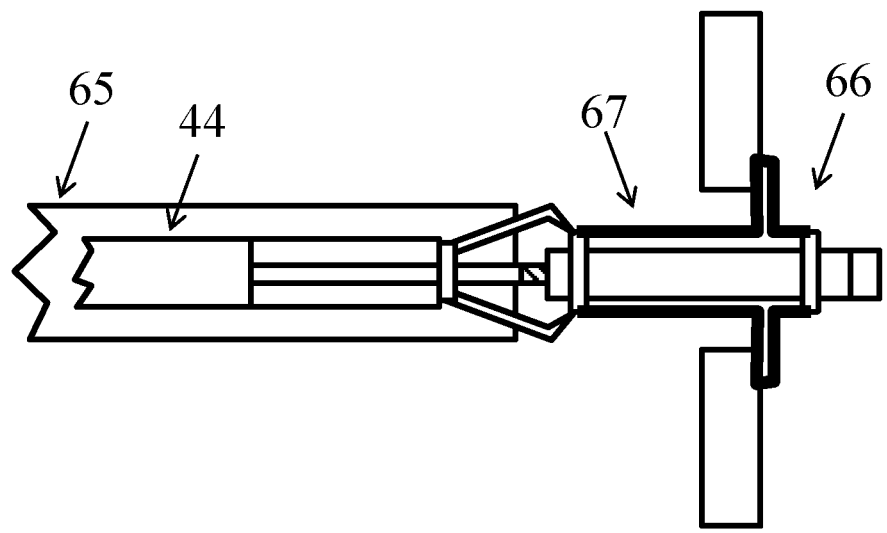
Figure 4J:
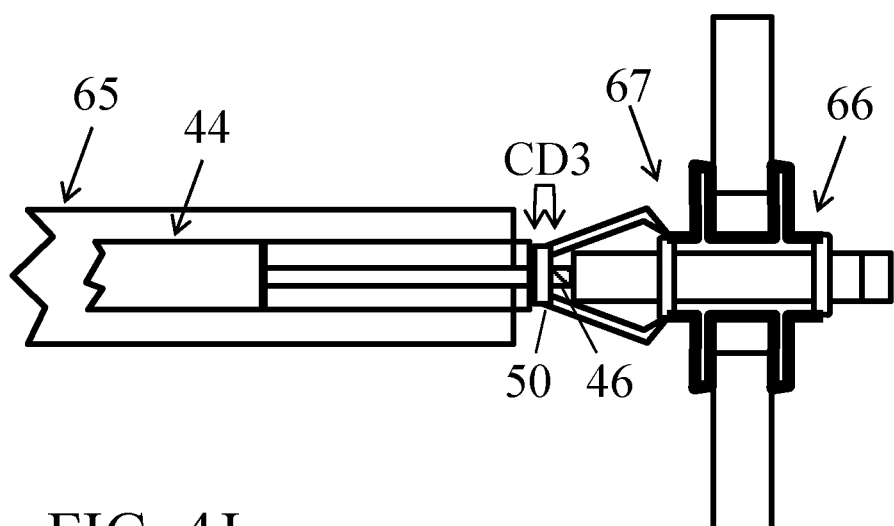
Figure 4K:
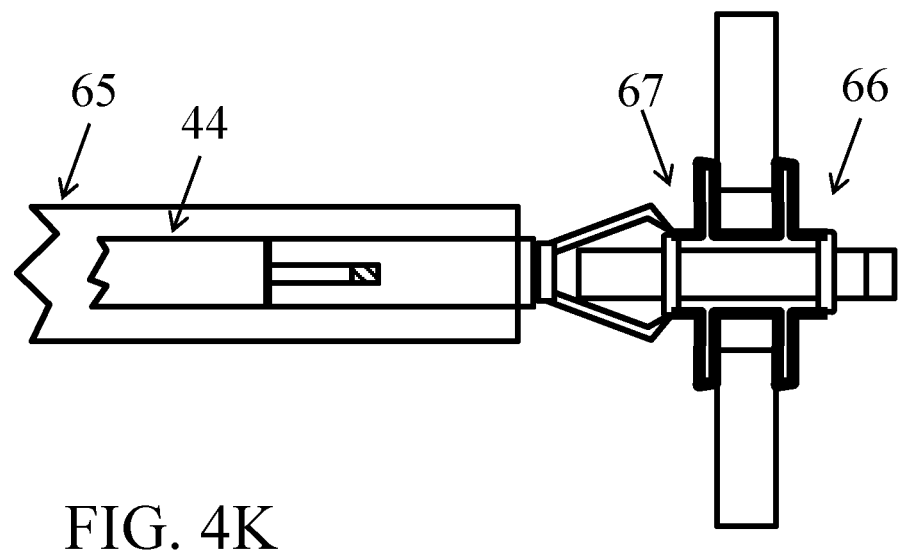
Figure 4L:
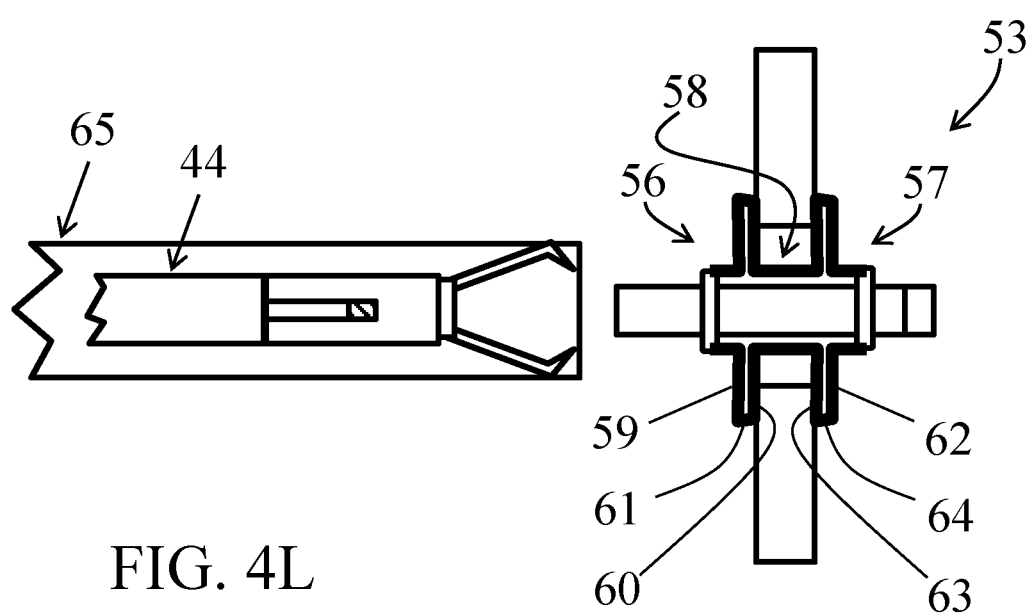
Figure 7A:
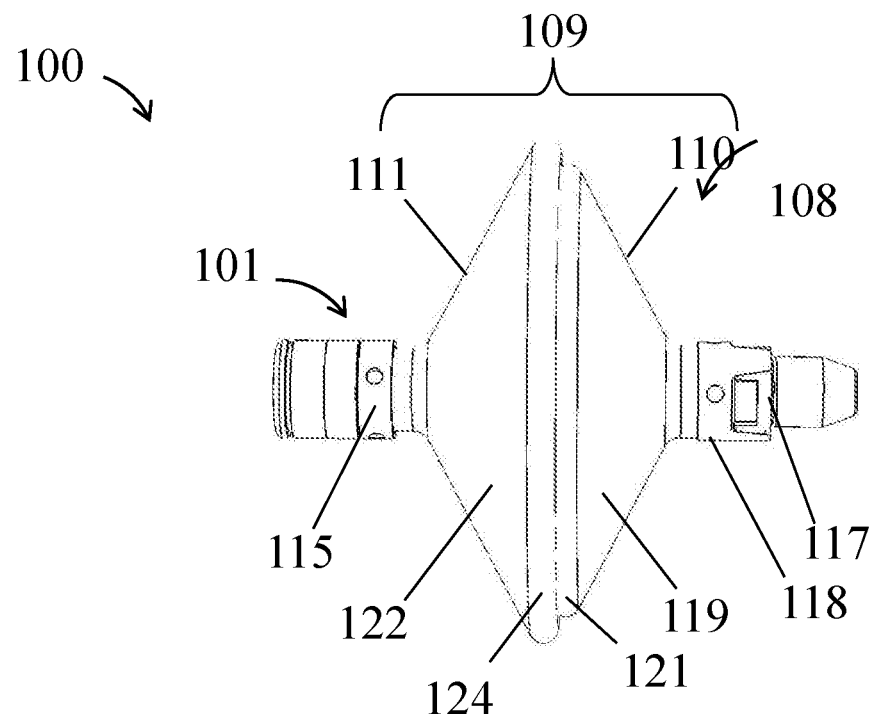
FIGS. 7A-7E are side or isometric views of an exemplary implant, the implant is having an implant body and a griping sleeve that forms a bellows structure when in the gripping form (FIGS. 7A-7C), the implant body is further having internal electronic components (FIGS. 7D-7E), in accordance with some embodiments of the invention.
Figure 7B:
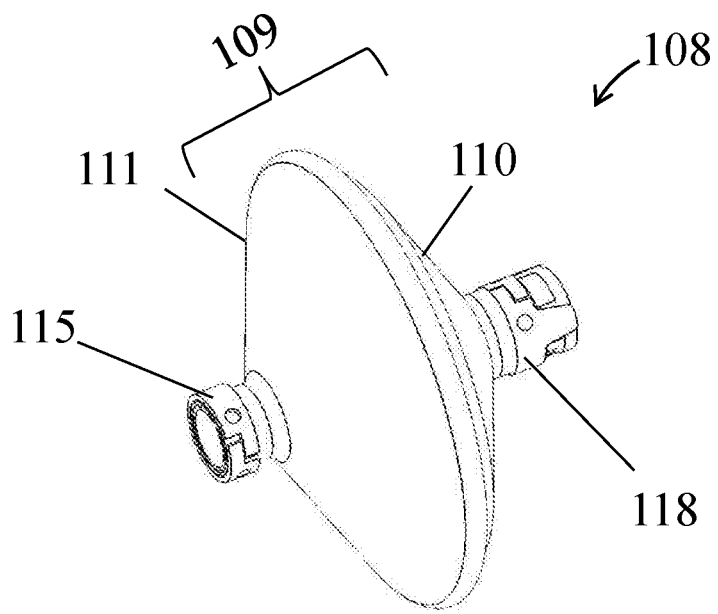
Figure 7C:
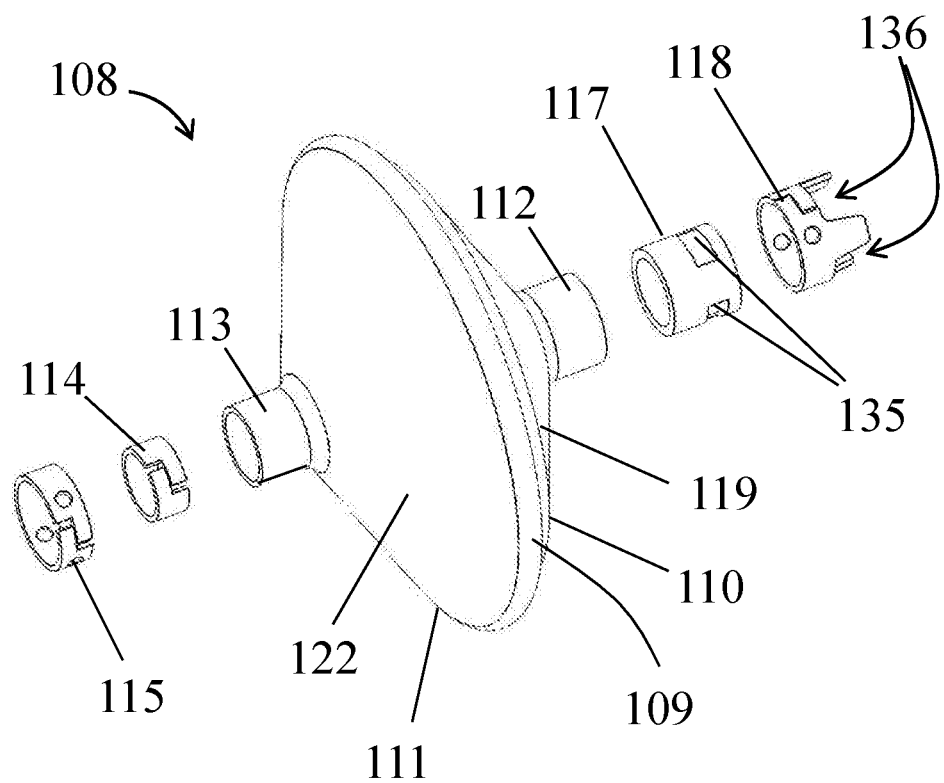
Figure 7D:
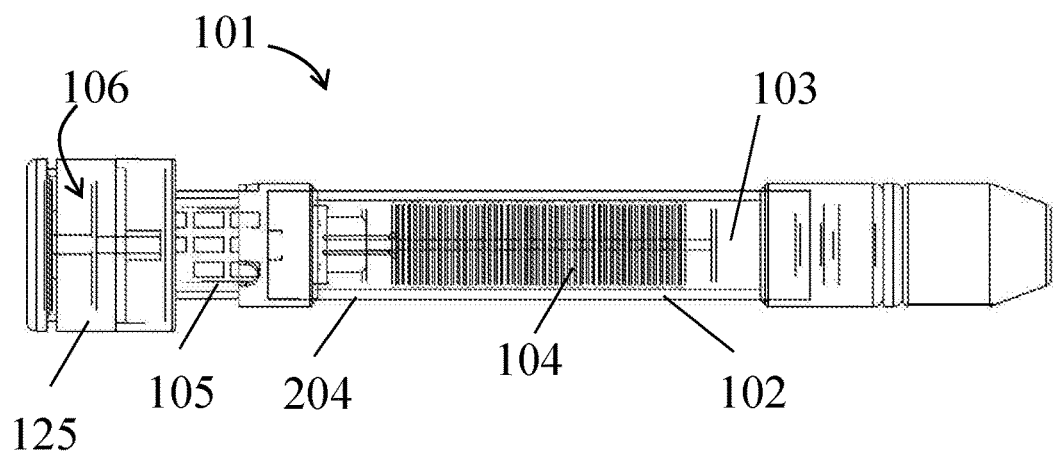
Figure 7E:
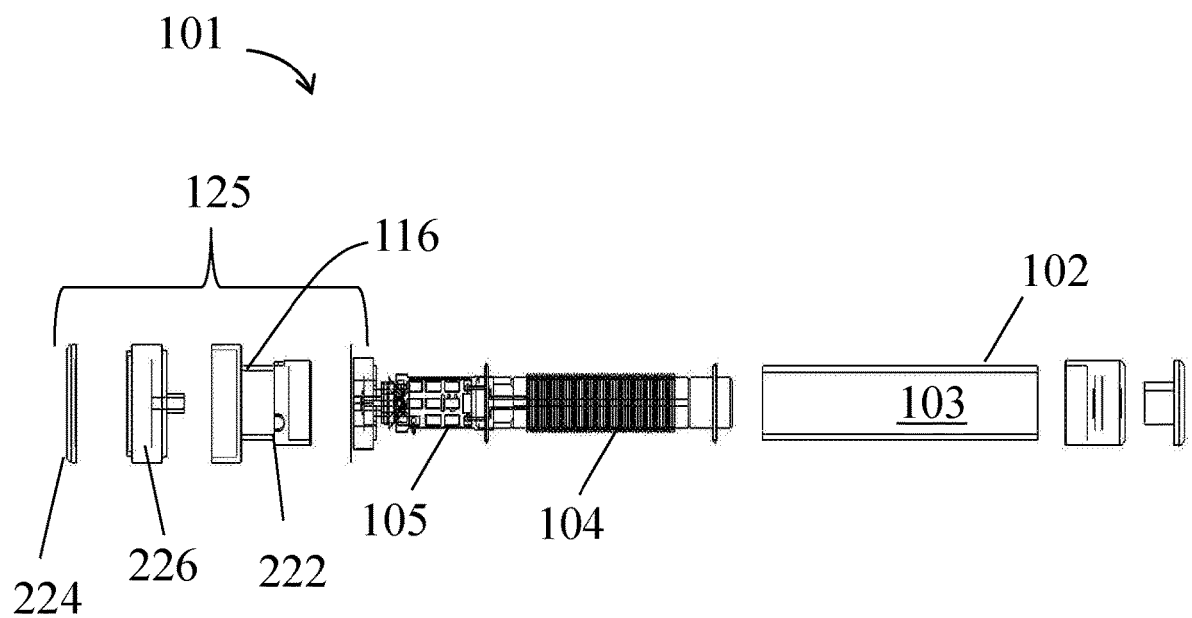

As shown for example in FIG. 4L, flexible gripping skirt 53 may have a preformed bellows-like structure with foldable units, including a proximal foldable unit 56 and a distal foldable unit 57, connected one with the other—either directly or with a non-foldable spacing unit 58, therebetween. Such spacing is sized or optionally sizable (e.g., stretchable in length) to compensate for width of the interatrial septum SW, similarly to as described with respect to spacing unit 31 shown in FIG. 3B.

When gripping sleeve 53 is subject to its gripping form, proximal foldable unit 56 forms a proximal wing extending outwardly-radially relative to implant body 42, so as to form a first proximal surface 59 and a second proximal surface 60 interconnected with a proximal edge 61. Likewise, distal foldable unit 57 forms a distal wing extending outwardly-radially relative to implant body 42, so as to form a first distal surface 62 and a second distal surface 63 interconnected with a distal edge 64. In some embodiments, implant 40 can be manipulated using implant deployment device 41 (with or without other means) to affect separately and distinctly each of proximal foldable unit 56 and distal foldable unit 57 (as for example in FIG. 4G showing folding of distal foldable unit 57 only).

Inner connector 46 is optionally connectable to inner connectee 47 by means of a screw arrangement. Outer connector 50 may be connectable to outer connectee 51 by means of a grasper arrangement which includes grasping jaws (with 2, 3, 4 or more jaws, optionally evenly distributed around outer member 49) configured for locking onto outer connectee 51, optionally having a mating recess pattern distributed circumferentially at tubular skirt proximal end 52, when the jaws are in a closed form. Optionally, the grasping jaws are configured in a normally closed form in absence of an opening force greater than a predetermined value. Outer connector 50 is rotationally fixable to outer connectee 51 (when connected thereto, e.g. by grasping or hooking to it), while allowing relative revolving of inner connector 46, thereby facilitating screwing or unscrewing of inner connector 46 and inner connectee 47.

In some embodiments, similarly to the use of outer member 49 (via outer connector 50) for disconnecting or connecting inner connector 46, the inner member 45 can be shaped or/and configured for disconnecting (e.g., forcedly opening jaws of) outer connector 50, when needed. As such, when outer connector 50 is connected to outer connectee 51 and inner connector 46 is released (disconnected with inner connectee 47), grasping jaws can be shifted from the [normally] closed form to an opened form by pressing inner member 45 against a lever mechanism in outer connector 50 arranged to thereby impose the grasping jaws to retract outwardly (an example of such mechanism is shown in FIGS. 11A-11D).

The implant deployment device 41 or/and implant 40 may be provided (e.g., as a kit) with means to select an operative portion of tubular skirt 53 and to restrict its manipulation (with the implant deployment device 41) only to the selected operative portion. Exemplary means of such sort may include an outer sheath 65 (shown in FIG. 4B for example), which may be used to pass implant 40 with deployment device 41 therethrough from entry point up to target location in subject's body, but can be particularly sized and configured also for restricting (e.g., constricting) selective portions of tubular skirt 53. In some such embodiments, deployment device body 44 is dimensioned to allow lengthwise sliding of outer sheath 65 thereon from a distal-most implant covering position (as shown in FIG. 4E), in which outer sheath 65 restricts expansion or/and compression of a distal portion 66 of tubular skirt 53, through an intermediate implant covering position (as shown in FIG. 4F), in which outer sheath 65 restricts expansion or/and compression of a proximal portion 67 of tubular skirt 53 and allows expansion or/and compression of distal portion 66 thereof, to a fully retracted position (as shown in FIG. 4I) in which implant 40/tubular skirt 53 is fully uncovered by outer sheath 65.

An exemplary method for sealing a wall opening ('WO') in a septal wall (such as 'SW') in a subject body is disclosed, by applying implant deployment device 41 in with implant 40, as an example. Optionally, alternatively or additionally, similar approach can be applied for fixating crosswise an elongated implant (such as implant 40) to an organ wall (such as septal wall SW) in a subject body. First, a route from an entry point to subject's vasculature is to the septal wall SW is set, and outer sheath 65 is passed therealong. In case wall opening WO is not readily present (e.g., as a defect in the atrial septum, as shown for example in FIG. 4B) it is first formed using dedicated instruments that can be provided via lumen of outer sheath 65 or other delivery conduit. FIGS. 5A-5B are schematic side cut views of a defected organ wall before and after deploying an exemplary implant 70 (which may be similar or identical to implant 20 or/and to implant 40), in accordance with some embodiments of the present invention. FIGS. 6A-6B are schematic side cut views of a body organ with an organ wall before and after deploying an exemplary sensory implant 80 (which may be similar or identical to implant 20 or/and to implant 40 or/and to implant 70), in accordance with some embodiments of the present invention.

As shown in FIGS. 4C-4E, implant 40 is provided attached to implant deployment device 41 and passed (via outer sheath 65) through the wall opening WO until a chosen distal portion 66 of tubular skirt 53 extends posteriorly (beyond) (i.e., in front of) septal wall WO and proximal portion 67 of tubular skirt 53 remains anteriorly before (i.e., behind) septal wall SW. Tubular skirt 53 may be constricted to extended narrow form with constricting means, such as with outer sheath 65. Optionally, alternatively or additionally, tubular skirt 53 is actively stretched lengthwise to the extended narrow form by relatively positioning outer connector 50 or/and inner connector 46 into a first connecting distance CD1 (FIG. 4D).

As shown in FIG. 4F, implant 40 is protruded out of outer sheath 65 (e.g., by pulling proximally the outer sheath as needed, optionally as under vision) such that tubular skirt distal portion 66 is unconstricted by the outer sheath 65 and tubular skirt proximal portion 67 remains constricted by the outer sheath.

As shown in FIG. 4G, while maintaining tubular skirt proximal portion 67 confined to extended narrow form, tubular skirt distal portion 66 is compressed to a first expanded form by at least partly regaining a first preformed shape (tubular skirt distal portion 66 may at least partly conform to outer boundaries of implant body 42 or/and of septal wall SW or/and to stresses imposed by tubular skirt proximal portion 67). Compressing tubular skirt distal portion 66 to first expanded form is facilitated by relatively positioning outer connector 50 or/and inner connector 46 into a second connecting distance CD2.

As shown in FIG. 4H, implant body 42 is pulled by the implant deployment device 41 so as to press tubular skirt distal portion 66 (in the first expanded form) against septal wall SW until reaching a chosen shaping thereof or/and until a chosen resistance magnitude is developable by the septal wall in response to the pulling, which can indicate to the medical practitioner a favorable implant positioning/stabilization, or/and covering of the wall opening WO with implant 40.

As shown in FIG. 4I, implant 40 is then further protruded out of outer sheath 65, such that both tubular skirt distal portion 67 and tubular skirt proximal portion 66 are unconstricted by outer sheath 65.

As shown in FIG. 4J, while maintaining tubular skirt distal portion 66 substantially in the first expanded form, tubular skirt proximal portion 67 is compressed to a second expanded form by at least partly regaining a second preformed shape (tubular skirt proximal portion 67 may at least partly conform to outer boundaries of the septal wall). Compressing tubular skirt proximal portion 67 to second expanded form is facilitated by relatively positioning outer connector 50 or/and inner connector 46 into a third connecting distance CD3. Gripping is optionally achieved by forcing proximal foldable unit 56 into forming proximal wing extending outwardly-radially relative to said implant body 42 and forcing distal foldable unit 57 into forming distal wing extending outwardly-radially relative to implant body 42. As such, implant deployment device 41 applies gripping against opposing ends of the septal wall SW around implant body 42, with tubular skirt distal portion 66 compressed to substantially its first expanded form and tubular skirt proximal portion 67 compressed to its substantially second expanded form, with sufficient force to maintain implant body 42 aligned across the septal wall SW.

As shown in FIGS. 4K and 4L, implant 40 can then be detached from implant deployment device 41 (after medical practitioner can check and determine deployment results), and implant deployment device 41 may then be removed, such as by pulling it out through outer sheath 65 or any other conduit. Detachment optionally includes separately and sequentially disconnecting inner connector 46 from said inner connectee 47 and outer connector 50 from outer connectee 51. Inner connector 46 (FIG. 4K) disconnecting is optionally particularly followed by disconnecting outer connector 50 (FIG. 4L). Reference is now made to FIGS. 7A-7E, which show different views of implant 100 (which may be similar in function or/and in structure, at least partly, to implant 20 or/and to implant 40 or/and to implant 70 or/and to implant 80). Implant 100 includes an implant body 101 having a tubular body wall 102 (shown in FIG. 7D, for example) and connected body segments. In some embodiments, implant 100 is configured for coupling onto a chamber wall in a subject body, and configured for inductive coupling with an external unit (such as external unit 11 of FIG. 1B) positionable outside the subject body, and for transmitting digital signals to the external unit. In some embodiments, body wall 102 encloses an inner lumen 103 (shown in FIG. 7E, for example) and configured for housing an RF antenna 104, an electronic circuit unit 105 or/and sensing means 106 (shown in FIGS. 7D and 7E, for example), which are configured for sensing, monitoring, or/and detecting, a condition in a chamber of the heart.

Implant 100 further includes a septum gripper 108 (shown, separately, in FIGS. 7B and 7C) including a flexible gripping sleeve 109. Flexible gripping sleeve 109 is optionally fixedly connected to implant body 101 with a distal inner ring and slidably connected to the implant body with an axially slidable proximal inner ring. Flexible gripping sleeve 109 is selectively shapeable from an extended delivery form, when the proximal inner ring is withdrawn proximally away from the distal inner ring, to a preformed gripping form encompassing the nonconductive wall section, configured for gripping onto the chamber wall, when the proximal inner ring is advanced distally towards the distal inner ring. Flexible gripping sleeve 109 may include an electrically conductive mesh covered with an electrically insulating layer, and each of the proximal and distal inner rings is made from an electrically nonconductive material.

Gripping sleeve 109 includes a bellows-like structure, with a plurality of the foldable units, namely, a proximal foldable unit 110 and distal foldable unit 111. Septum gripper 108 further includes a proximal non-foldable sleeve portion 112 disposed proximally to the proximal foldable unit 110, and a distal non-foldable sleeve portion 113 disposed distally to the distal foldable unit 111 (shown in FIG. 7C, for example).

Distal non-foldable sleeve portion 113 is sandwiched between a sleeve fixation inner ring 114 and a sleeve fixation outer ring 115. According to some embodiments, sleeve fixation inner ring 114 is sized and shaped to mate or/and lock in a recess 116 (shown in FIG. 7E) in implant body 101, which forms a sleeve fixation area and prevents axial and rotation movement of distal non-foldable sleeve portion 113 during transformation (reshaping or/and motion) of septum gripper 108.

Proximal non-foldable sleeve portion 112 is sandwiched between a sleeve deploying inner ring 117 and a sleeve deploying outer ring 118. As will be explained in more details below, sleeve deploying inner ring 117 and sleeve deploying outer ring 118, and proximal non-foldable sleeve portion 112 sandwiched therebetween, are configured to selectively slide axially along implant body wall 102, as part of implantation of implant 100.

Figures 8A, 8B:
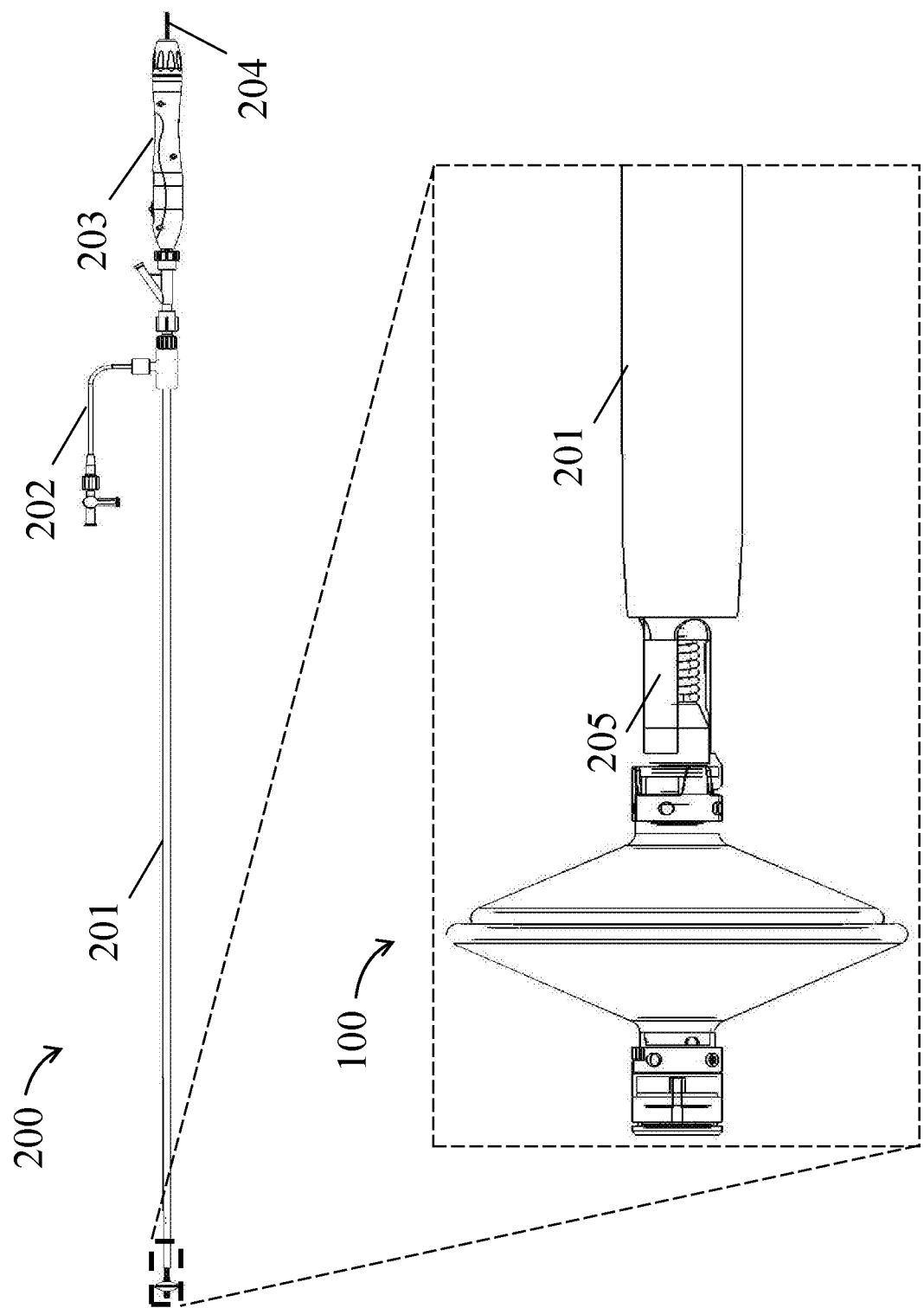
Figure 8C:
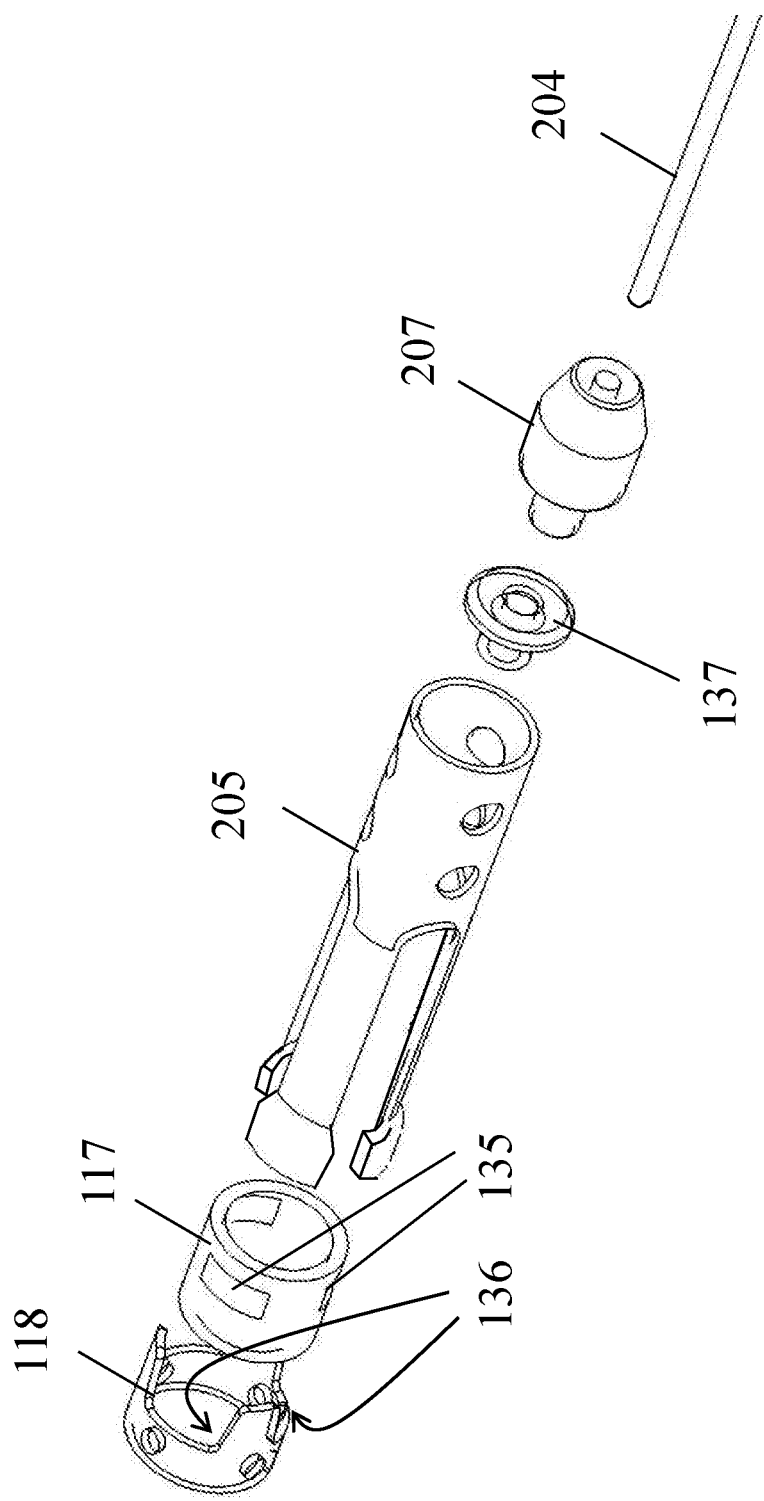

Gripping sleeve 109 is configured such that in the gripping form, the proximal foldable unit 110 forms a proximal wing extending outwardly-radially relative to implant body 101 so as to form a first proximal surface 119 and a second proximal surface 120 (as shown in FIG. 8E) interconnected with a proximal edge 121. Similarly, gripping sleeve 109 is configured such that in the gripping form, distal foldable unit 111 forms a distal wing extending outwardly-radially relative to implant body 101 so as to form a first distal surface 122 and a second distal surface 123 (as shown in FIG. 8E) interconnected with a distal edge 124.

Gripping sleeve 109 is further configured such that the plurality of foldable units 110 and 111 are configured for gripping by pressing the second proximal surface 120 or/and the proximal edge 121 against a proximal side of an atrial septum and pressing the second distal surface 123 or/and the distal edge 124 against a distal side of the atrial septum, under a continuous compression force greater than a predetermined minimal force value. As used herein the term "continuous compression force" relates to a continuous compression force applied by the foldable units 110 and 111 of the gripping sleeve 109 on the atrial septum. According to some embodiments, the gripping sleeve 109 is configured such to continuously for long periods, for example a year or so compress the atrial septum. The continuous compression force is greater than a predetermined minimal force taken, for example, from between about 0.1 gr and about 100 gr, optionally particularly between about 0.5 gr and about 50 gr, optionally particularly from about 1 gr and about 10 gr.

According to some embodiments, the bellows-like structure of foldable units 110 and 111 is configured with a coefficient of static friction chosen so as to prevent relative motion of the septum gripper 108 relative to the atrial septum under normal stresses (i.e., physiological stresses) applied thereto in the chamber of the heart.

According to some embodiments, when gripping sleeve 109 is in the gripping form, the first proximal surface 119 and the second proximal surface 120 are formed as nested conic structures extending proximally away from the proximal edge 121 separated by the proximal edge 121. According to some embodiments, when gripping sleeve 109 is in the gripping form, the first distal surface 122 and the second distal surface 123 are formed as nested conic structures extending distally away from the distal edge 124 separated by the distal edge 124.

Reference is now made to FIGS. 8A-8G which show use of an implant deployment device 200 for the delivery and deployment of implant 100, releasably connected thereto. Implant deployment device 200 optionally includes or is provided in an outer sheath 201, connectable with an inlet 202 (optionally used for delivering fluid, instrumentation, guide wire, optical fiber etc.) communicating with interior of outer sheath 201, an implant delivery loader 203, and an inner member 204, optionally in a form of a rod or a tether. Implant deployment device 200 may further include an outer connector 205 in a form of elastic jaws or arms, configured for releasably coupling with septum gripper 108 and thereby applicable for shifting septum gripper 108 between the delivery form and the gripping form by unhindered sliding along a segment of body wall 102 of implant 100 or/and of outer periphery of sheath 201. Optionally the outer connector 205 has a smooth surface. Implant deployment device 200, via inner member 204, is attached to the proximal end of implant body 201, and can be used for maintaining the implant body 201 in place when outer connector 205 is put to motion in order to achieve relative motion between the septum gripper 108 and implant body 101.

Inner member 204 is connectable to implant body 101 optionally with an inner connector 207, optionally in a form of a threading component threadable into a mating threading part 137 connected to or is part of proximal end of implant body 101. When connected to implant 100 with both inner member 204 and outer connector 205, the implant deployment device 200 can be used for deploying and fixating implant 100 within the heart septum. Outer connector 205 may then be applied for grasping the septum wall using septum gripper 108. The Outer connector 205 may then be released from septum gripper 108, prior to, followed by or in parallel to disconnecting inner member 204 from proximal end of implant body 101, once the implant has been positioned.

Outer connector 205 is releasably coupled to implant 100 at recesses 135 provided on sleeve deploying inner ring 117 of septum gripper 108. In some embodiments, sleeve deploying inner ring 117, when coupled with outer connector 205 and during deployment of septum gripper 108, is configured as a sliding element, optionally having a smooth surface in contact with implant body 101. In some embodiments, sleeve deploying inner ring 117 is also made from a nonconductive material.

As detailed above, a free end of gripping sleeve 109 is sandwiched with interconnecting sleeve deploying inner ring 117 and sleeve deploying outer ring 118, wherein the sleeve deploying outer ring 118 is crown-like shaped with proximally pointing concavities 136 for uncovering recesses 135 (when connected thereto above) for facilitating coupling of outer connector 205.

According to some embodiments, and as will be explained below, gripping sleeve 109 is fixedly extendable or/and compressible to a chosen length or/and shape in between more than two distinct forms, including a delivery form and a gripping form, when coupled with a distal end of the implant deployment device 200. According to some embodiments, septum gripper 108 coupling to the delivery system 200 enables full control on the deployment of the gripper 108. Such control affords selective positioning of the foldable units 110 and 111, separately, while their design optionally allows some degree of conformity in response to local anatomy or/and external stresses (e.g., applied by anatomy of the heart).

Figure 8F:
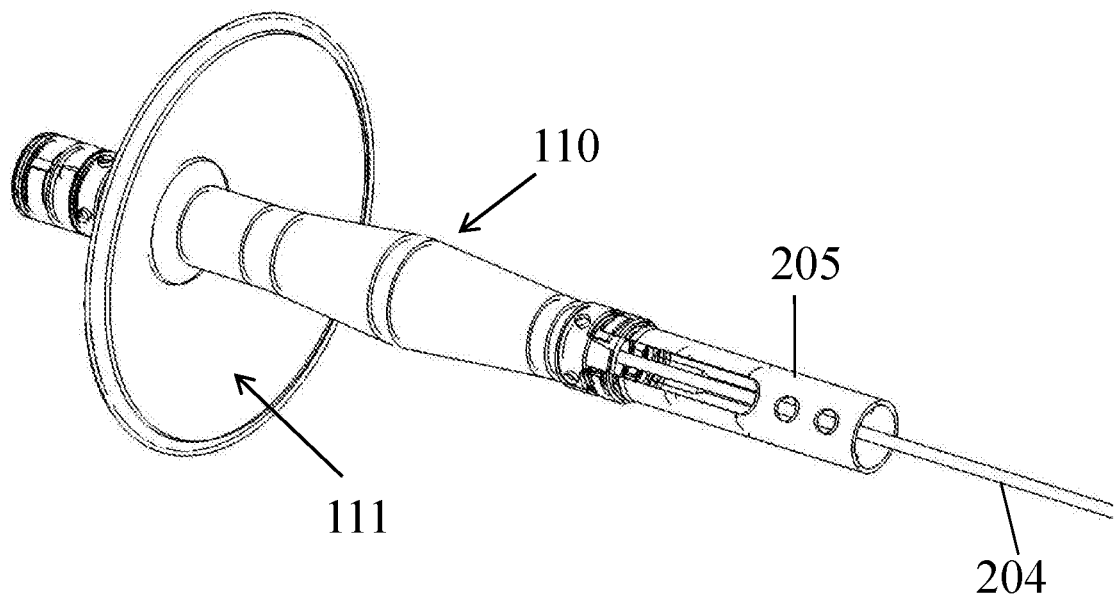
Figure 8G:
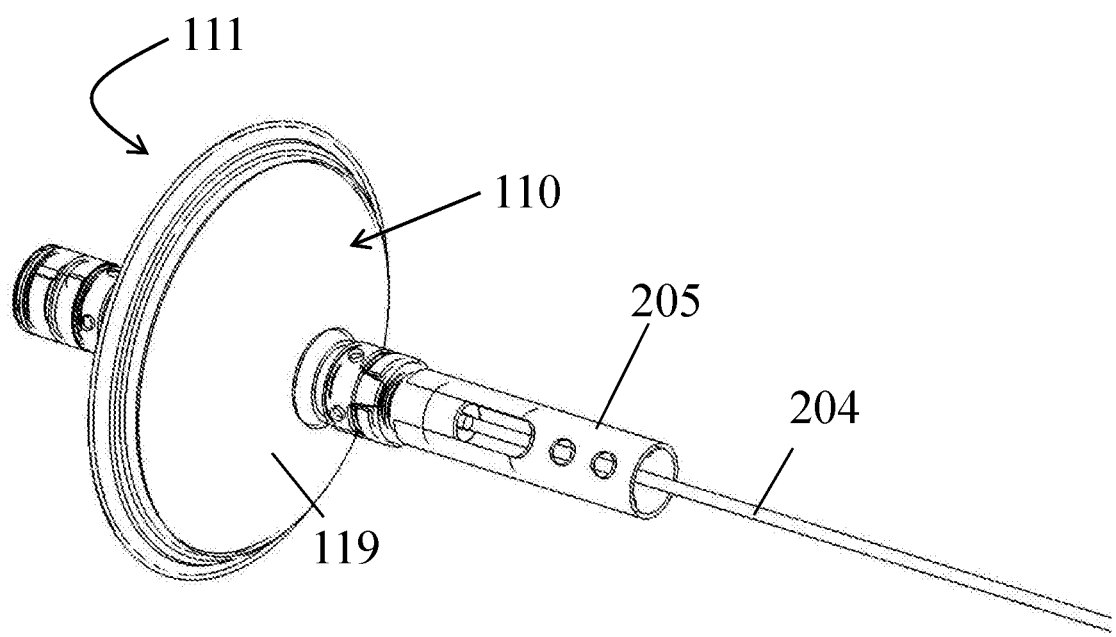

The procedure of implanting implant 100 within the atrial septum includes puncture and forming of a septum opening using any standard trans septal puncturing kit and in according to the normal procedure. The puncturing is associated with routing and inserting, for example, a lead including a punctuator through the septum for effecting opening within the septum. Implant deployment device 200 connected to implant 100 is then routed through the septum opening. When in the delivery configuration, gripping sleeve 109 of septum gripper 108 is extended to be sized for passing through the septum opening. Gripping sleeve 109 is thus forced to stretch or/and confined with an outer boundary having an outer boundary inner diameter. As the implant is inserted to protrude into the left atrium, when in the delivery configuration, the distal foldable unit 111 is first to be deployed (FIG. 8F). Following stabilization of the distal foldable unit 111 against the left atrial septum wall, the deployment device is stabilized to facilitate deployment of the proximal foldable unit 110 against the right atrial septum wall. Consequently, shifting from the delivery configuration to the gripping configuration (i.e., a non-bounded preformed gripping form) includes gripping of the griping sleeve 109 onto the atrial septum.

The implant body 101 is further fixated to or/and stabilized within the septal walls in a chosen orientation. As used herein the term "chosen orientation" refers to the orientation of implant 100 that the physician chooses for gripping the atrial septum by the gripping sleeve 109. Chosen orientation is a tridimensional orientation relative to a center point of the septum opening and includes implant body extending through the septum opening such that an operational member thereof (i.e., sensing means) is provided in the target chamber of the heart.

The implant 100 may be retrieved, if and when necessary in a manner similar to the deployment of the implant with the exception that the foldable units 110 and 111 are unfolded. Specifically, the proximal foldable unit 110 is firstly unfolded and thereafter the distal foldable unit 111 is unfolded to thereby afford retrieval and removal of the implant from the body.

Figure 9:
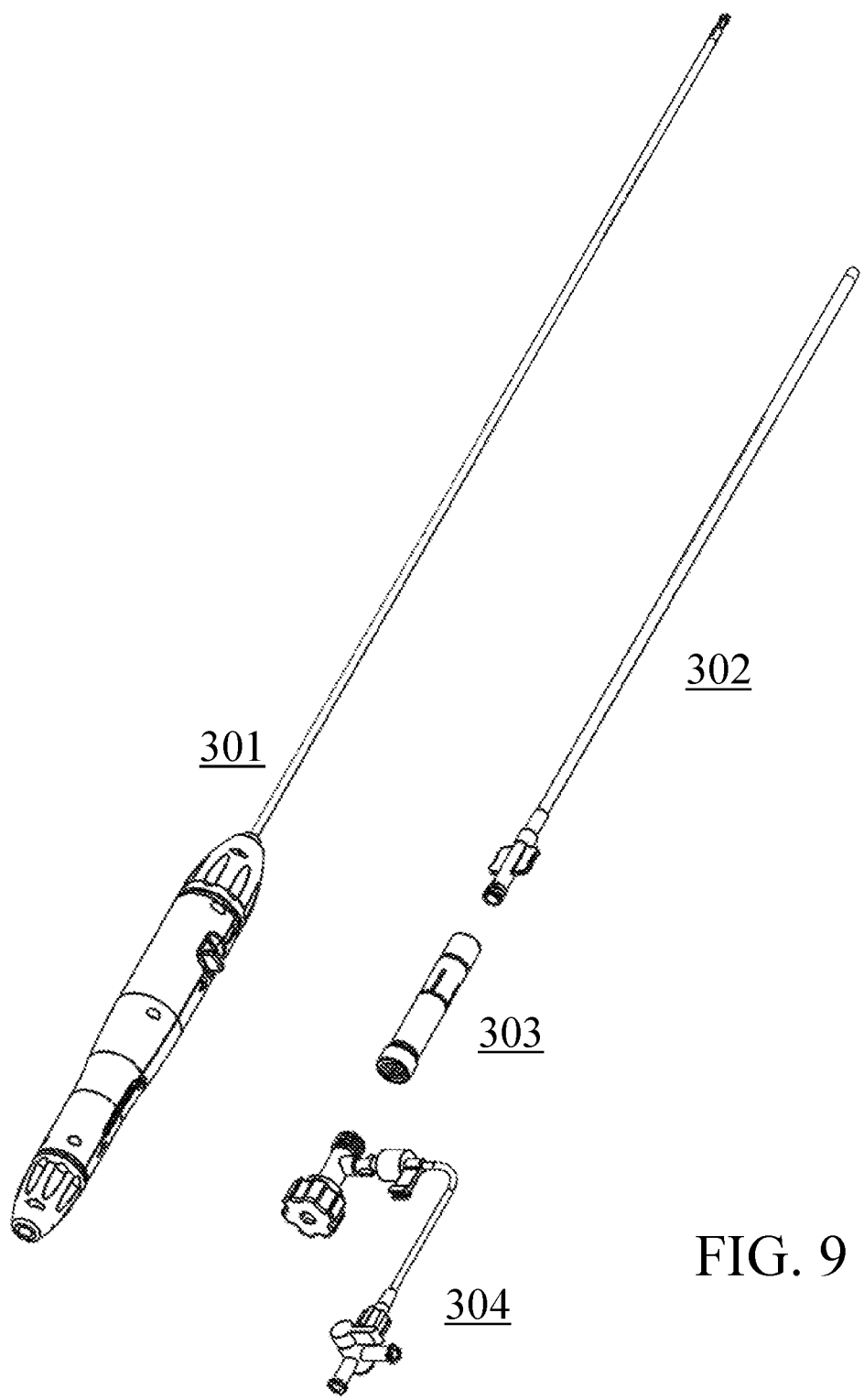
FIG. 9 is an isometric view of an exemplary set of tools for delivery and deployment of an implant, in accordance with some embodiments of the invention.

FIG. 9 is an isometric view of another exemplary set of tools for delivery, deployment or/and fixation of implant 100 across an organ wall, in accordance with some embodiments of the invention. Organ wall may be in a form of a septal wall, such as an atrial septum between right and left atria. Implant 100 can be deployed and fixated for sealing a wall opening in the organ wall or/and for facilitating continuous sensing or/and measuring conditions/parameters (e.g., pressure change) in the wall-closed organ. The exemplary set of tools includes, besides implant 100, an implant deployment device 301, an outer sheath 302, an implant loader 303 and a loader cap 304. Outer sheath has an outer diameter sized to pass and navigate through subject vasculature and a lumen sized to pass therethrough implant deployment device 301 and the implant 100 in its narrowed and stretched delivery form. Implant loader 303 is configured for facilitating easy and safe introduction of the implant 100 into the constricting lumen of outer sheath 302 and as such may include a funnel-like gradually converging lumen for gradually constricting the implant septum gripper (tubular skirt) to its final stretched/narrowed form. Therefore, implant 100 may first be connected (or provided readily connected) to implant delivery device 301 (cap 304 may be loaded on to deployment device body/shaft before then), then optionally be fully or partially stretched by the implant deployment device 301, then introduced via loader 303 into outer sheath 302. Afterwards, loader 303 can be capped with cap 304.

FIGS. 10A-10E are isometric views of implant deployment device 301 and steps in an exemplary method for deploying an implant such as implant 100 with the set shown in FIG. 9. FIG. 11 shows a sequence of side cut views of an exemplary implant deployment device (distal portion) and steps in an exemplary method for deploying an implant. Implant deployment device 301 includes a handle 305, a sheath spacer 306, a deployment device body (shaft) 307, controls (controllers) including a distal knob 308 and a proximal knob 309, and a safety switch 310 (as shown for example in FIG. 10A(I)).

Deployment device body 307 includes (houses) a rod-like inner member 311 and a tube-like outer member 312, shown for example in FIG. 11(I), which can slide lengthwise (proximally/distally) relative to each other by turning distal knob 308 clockwise or counterclockwise. Inner member 311 may be covered with a compression spring 313 in order to increase stiffness to connectivity with implant 100. Inner member 311 ends with an inner connector 314 which is detachably connected (screwed) with a mating inner connectee (for example threading part 137 shown in FIG. 8C) provided in proximal end of implant body. Outer member 312 ends with an outer connector 315 which is detachably connected (grasping) with a mating inner connectee (for example recesses 135 shown in FIG. 8C) provided in proximal end of septum gripper (tubular skirt).

Figure 10A:
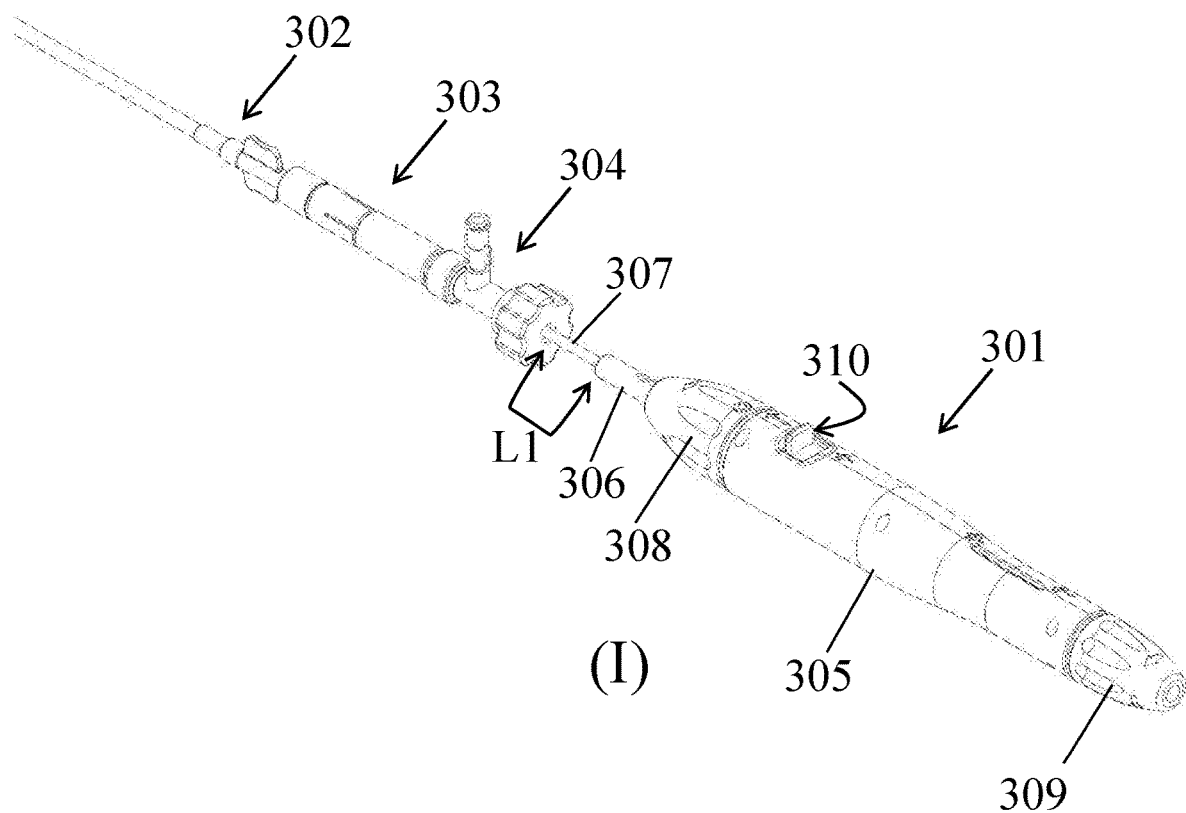
FIGS. 10A-10E are isometric views of an exemplary implant deployment device and steps in an exemplary method for deploying an implant, in accordance with some embodiments of the invention.
Figure 10A:
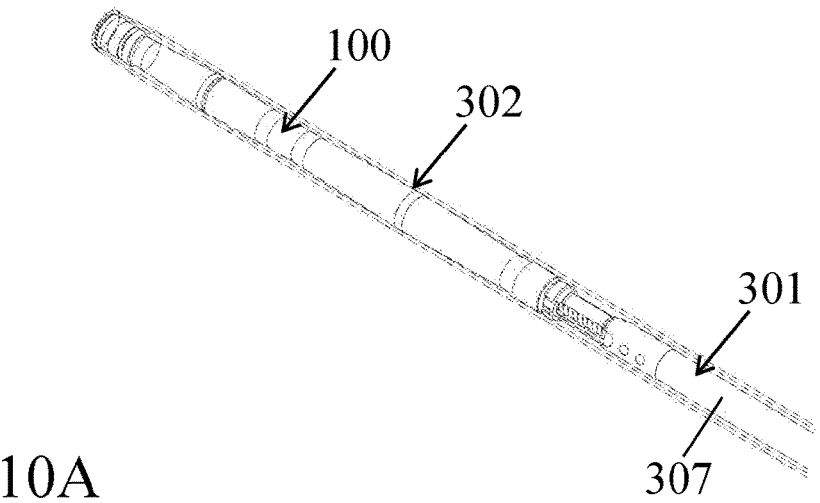
Figure 11:
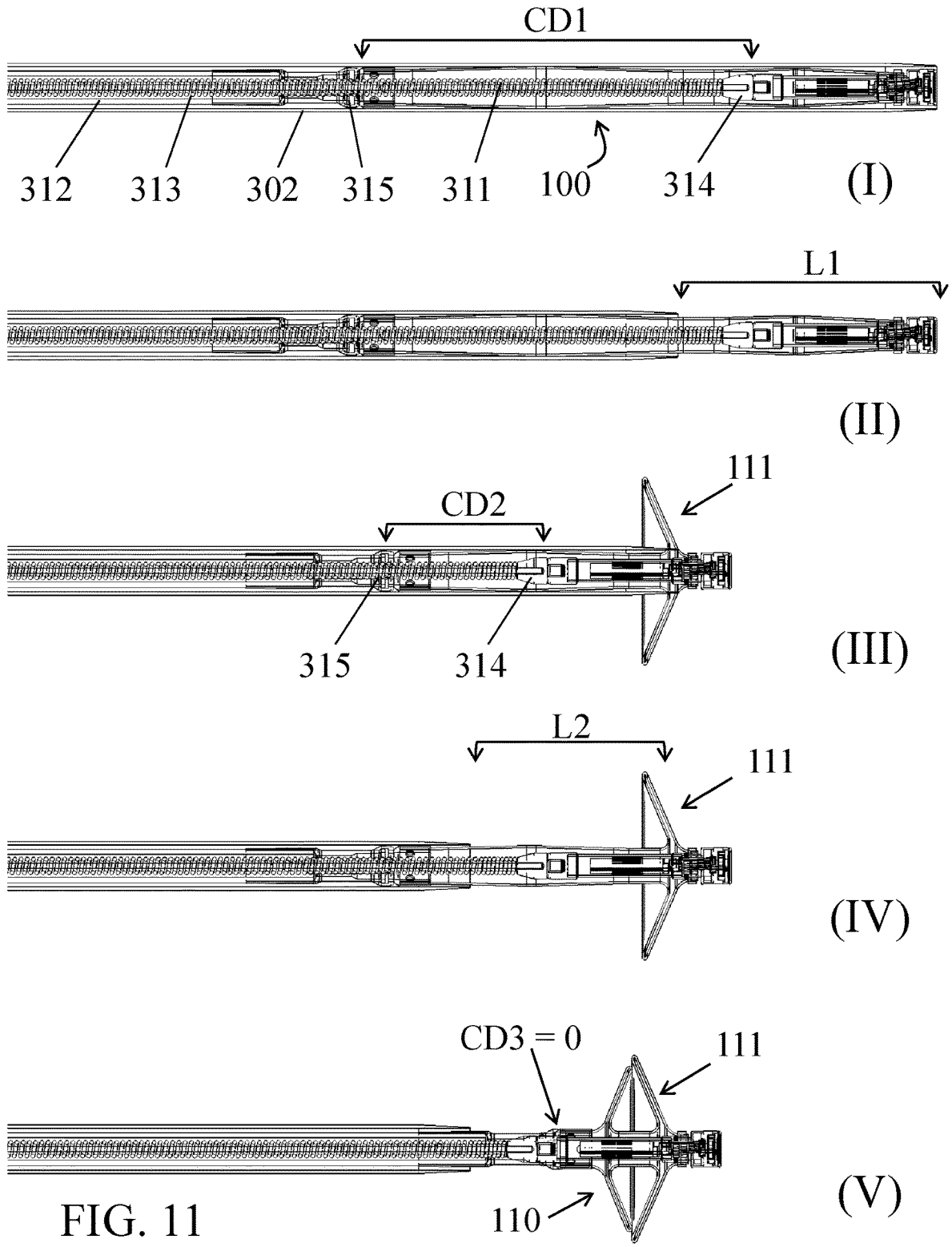
FIG. 11 shows a sequence of side cut views of an exemplary implant deployment device (distal portion) and steps in an exemplary method for deploying an implant, in accordance with some embodiments of the invention.

FIG. 10A and FIG. 11(I) show a scenario (equivalent to the scenario shown in FIG. 4E), in which implant 100 is provided (e.g., restricted or constricted) at distal portion of outer sheath 302. Implant 100 is in the stretched-narrowed form when inner connector 314 and outer connector 315 are distant with each other by first connecting distance CD1. The set may be configured such that the implant is fully covered by outer sheath 302 and provided exactly adjacent to distal tip of outer sheath 302 as long as cap 304 proximal surface is distanced from sheath spacer 306 by a first predetermined distance being exactly L1. In this example, sheath spacer 306 is at its fully protruding extent, as shown, when distal knob 318 is fully rotated clockwise (considering axis of rotation is projected along device's longitudinal axis directed from proximal to distal).

Figure 10B:
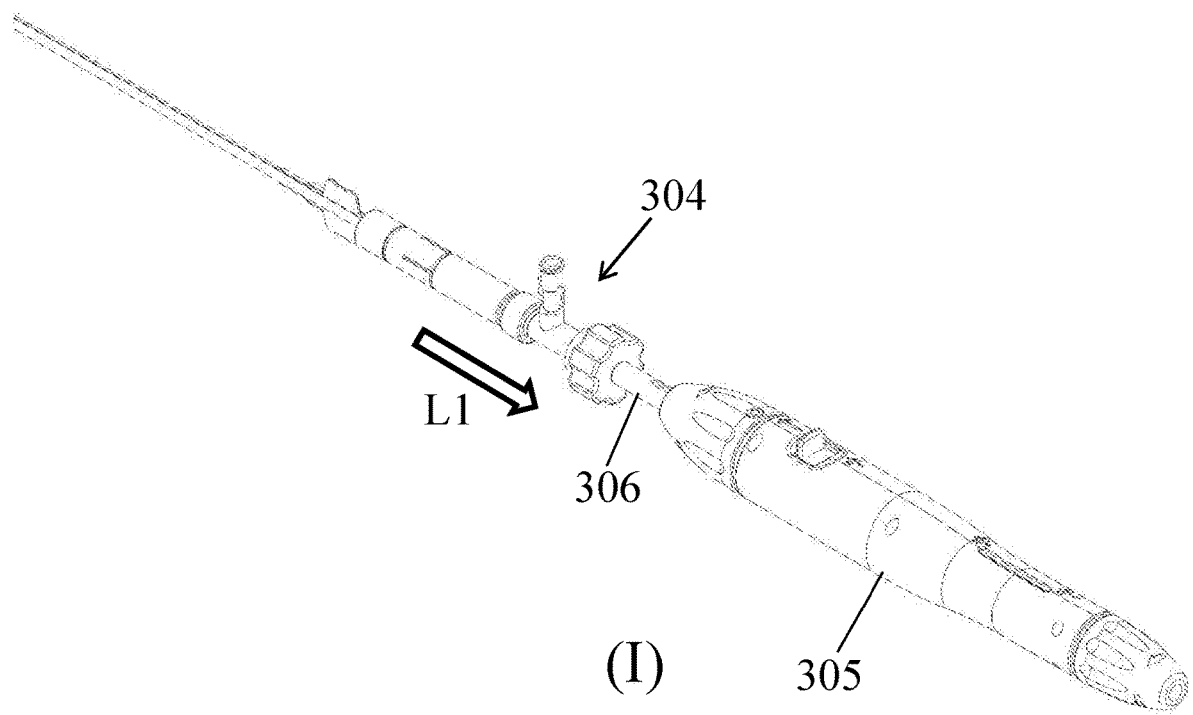
Figure 10B:
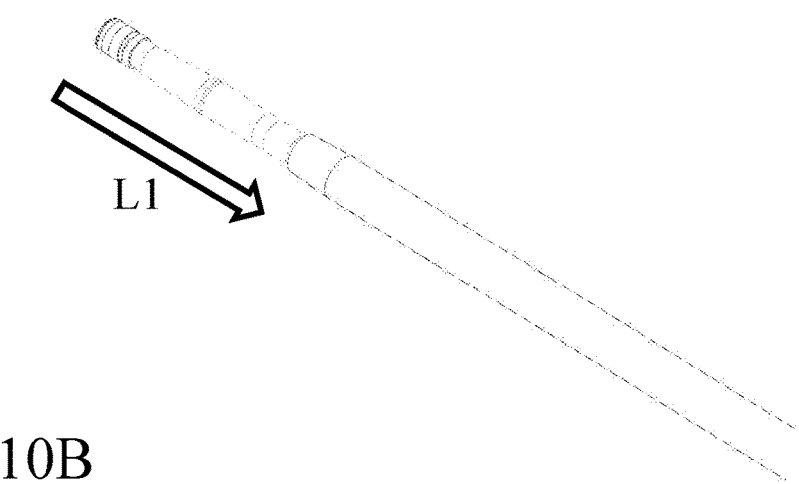

FIG. 10B and FIG. 11(II) show a scenario (equivalent to the scenario shown in FIG. 4F), in which outer sheath 302 is withdrawn by a length equal to L1, thereby exposing distal portion of septum gripper (tubular skirt) of implant 100, which is equal or greater in length than distal foldable unit 111, while maintaining proximal foldable unit 110 stretched and covered in outer sheath 302. Retraction of outer sheath 302 can be done manually by simply pulling cap 304 until it is in contact with sheath spacer 306.

Figure 10C:
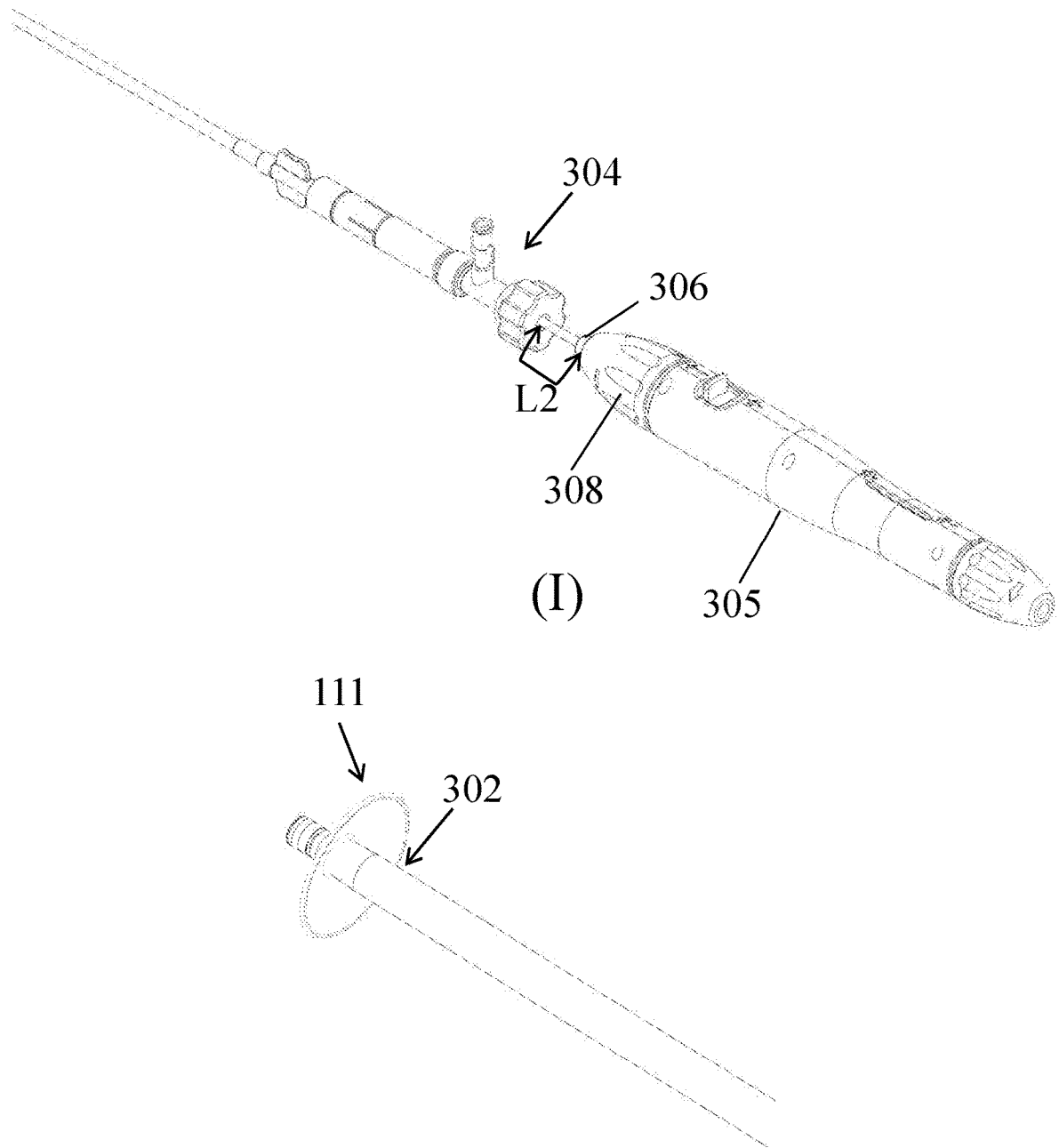

FIG. 10C and FIG. 11(III) show a scenario (equivalent to the scenario shown in FIG. 4G), in which inner connector 314 and outer connector 315 are in a second (shorter) connecting distance CD2 with each other, thereby forcing distal foldable unit 111 to substantially regain its preformed gripping form. Proximal foldable unit 110 is maintained stretched and narrowed as it is kept restricted/constricted by outer sheath 302. Shifting from first connecting distance CD1 to second connecting distance CD2 is achieved by revolving distal knob 308 counterclockwise (in this example) until connecting distance CD2 is met (optionally by restricting further knob revolving using a stop at a predefined angle). Implant deployment device 301 is configured such that sheath spacer 306 is fully retracted when distal knob 308 is revolved until connecting distance CD2 is met, thereby allowing a further manual retraction of outer sheath 302 (or, alternatively, pushing forward implant deployment device 301 relative to outer sheath 302, or any combination of device 301 pushing and sheath 302 pulling), by an exact distance equal to L2.

Figure 10D:
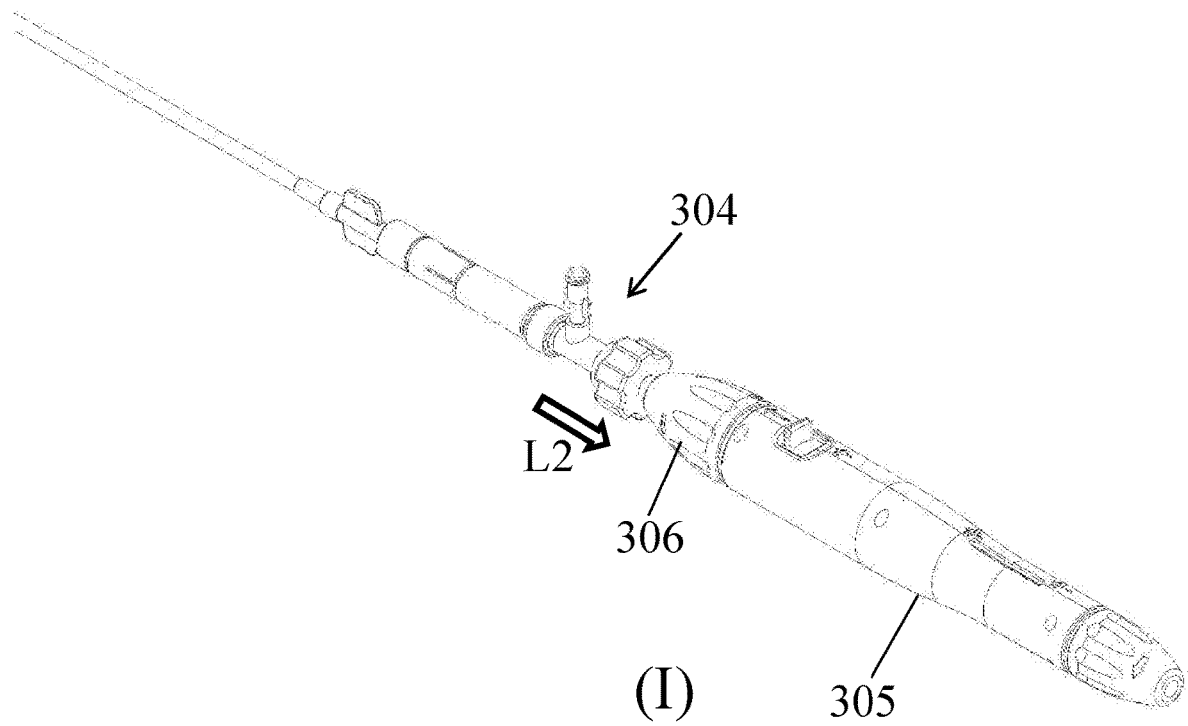
Figure 10D:
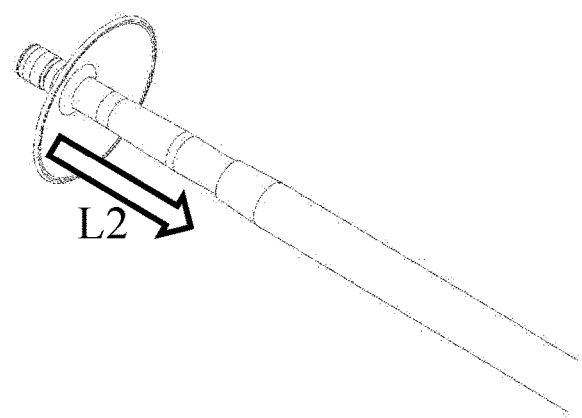

FIG. 10D and FIG. 11(IV) show a scenario (equivalent to the scenario shown in FIG. 4I), in which outer sheath 302 is withdrawn by a length equal to L2, thereby exposing proximal portion of septum gripper (tubular skirt) of implant 100, which is equal or greater in length than proximal foldable unit 110. Outer sheath 302 can be withdrawn manually by pulling cap 304 (or pushing handle 305 forward) until it is in contact with sheath spacer 306 or with handle 305, for example.

Figure 10E:
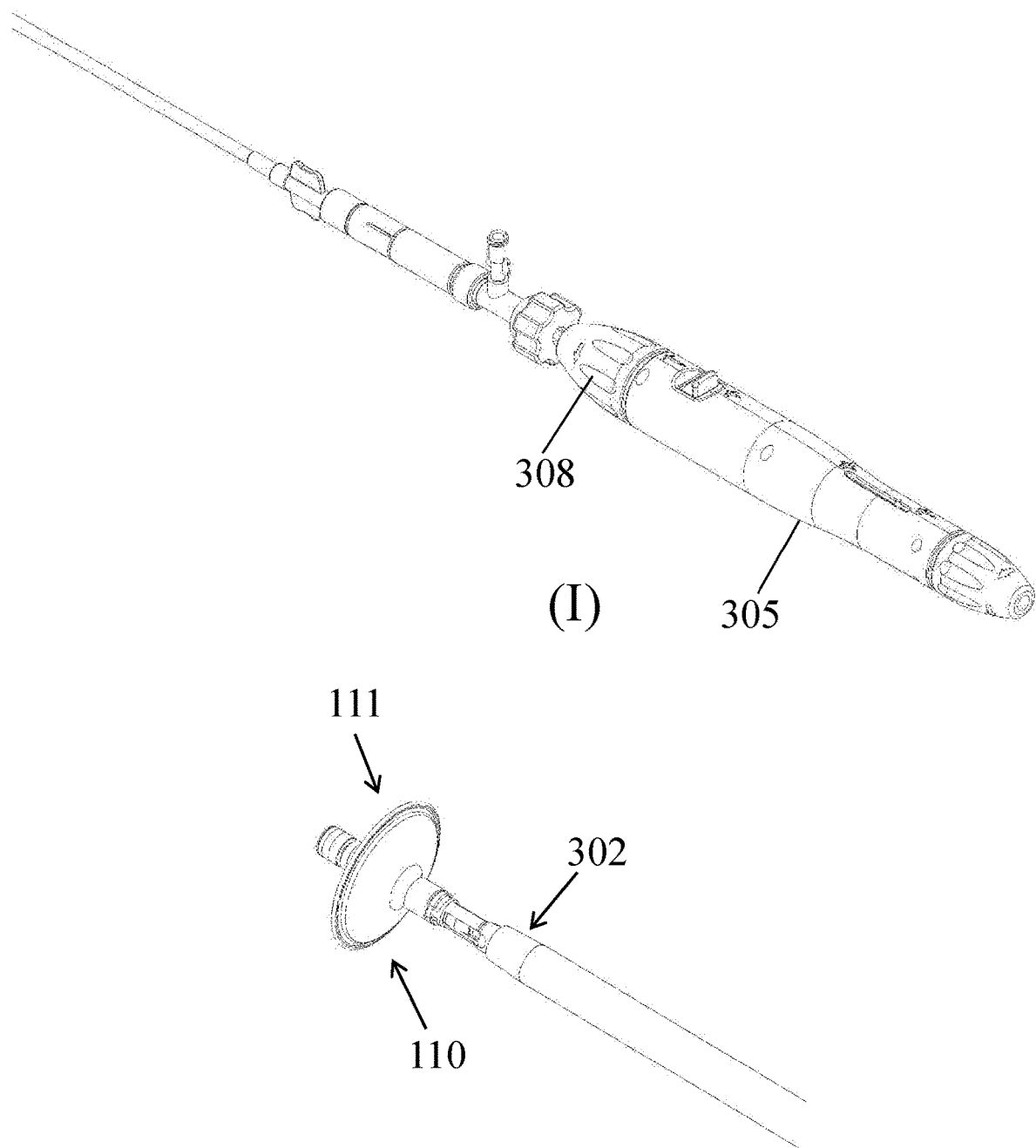

FIG. 10E and FIG. 11(V) show a scenario (equivalent to the scenario shown in FIG. 4J), in which inner connector 314 and outer connector 315 are in a third (shorter) connecting distance CD3 with each other, which is substantially null in this example, thereby forcing proximal foldable unit 110 to substantially regain its preformed gripping form, thereby forming with proximal foldable unit 110 the overall preformed gripping form of the septum gripper. Shifting from second connecting distance CD2 to third connecting distance CD3 is achieved by further revolving distal knob 308 counterclockwise (in this example) until connecting distance CD3 is met (optionally by restricting further knob revolving using a stop at a predefined angle). Safety switch 310 must be activated (e.g., mechanically switched from distal position to proximal position, as shown in the figures), in this example, in order to be able to further revolve distal knob 308 counterclockwise after connecting distance CD2 has been met.

As shown, the implant deployment devices of the invention can achieve full deployment of organ wall/septum gripping type implants (such as implants 20, 40, 70, 80 and 100) even without any interaction with the anatomy, which is believed to be unique in view of current practice and means, where septal wall anatomy and wall opening boundaries play critical role in septal implants (e.g., septal occluders) deployment (such as by using counteracting or/and friction forces applied by the anatomy onto the deployment instrumentation, for example in order to extract the implant and allow it to regain its final deployed shape. Proposed methods and means (devices) allow fully controlled, sequential, anatomy-independent, deployment and fixation of septum gripping implants of the invention.

Figure 12A:
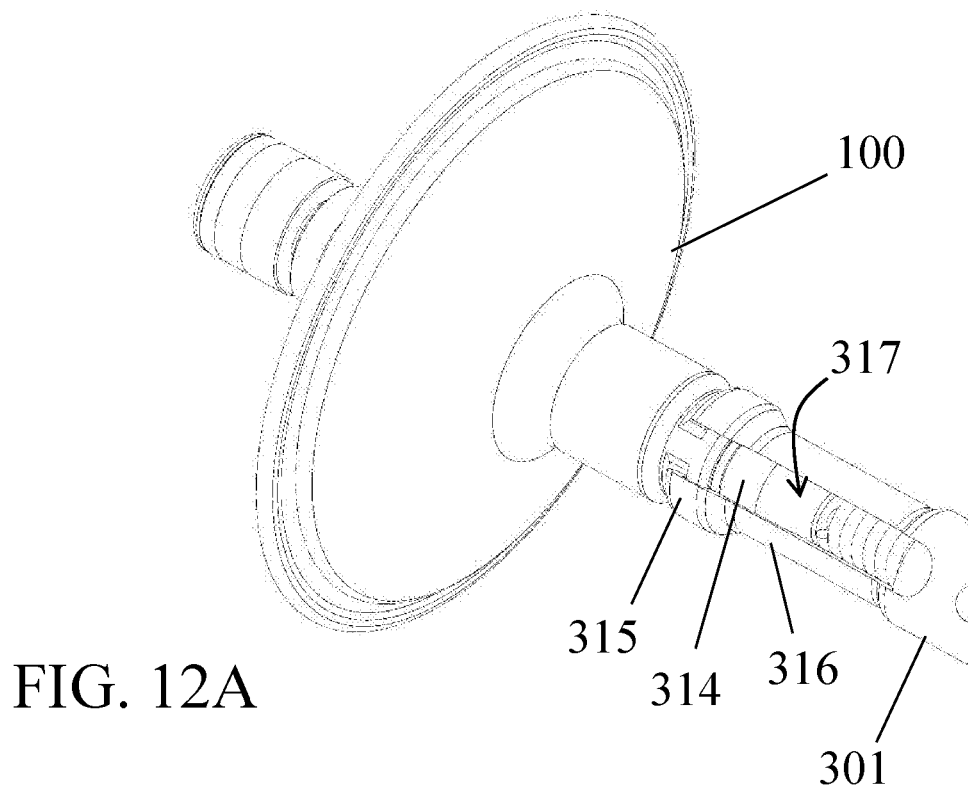
FIGS. 12A-12D are isometric views of an exemplary implant deployment device and steps for disconnecting from an implant, in accordance with some embodiments of the invention.
Figure 12B:
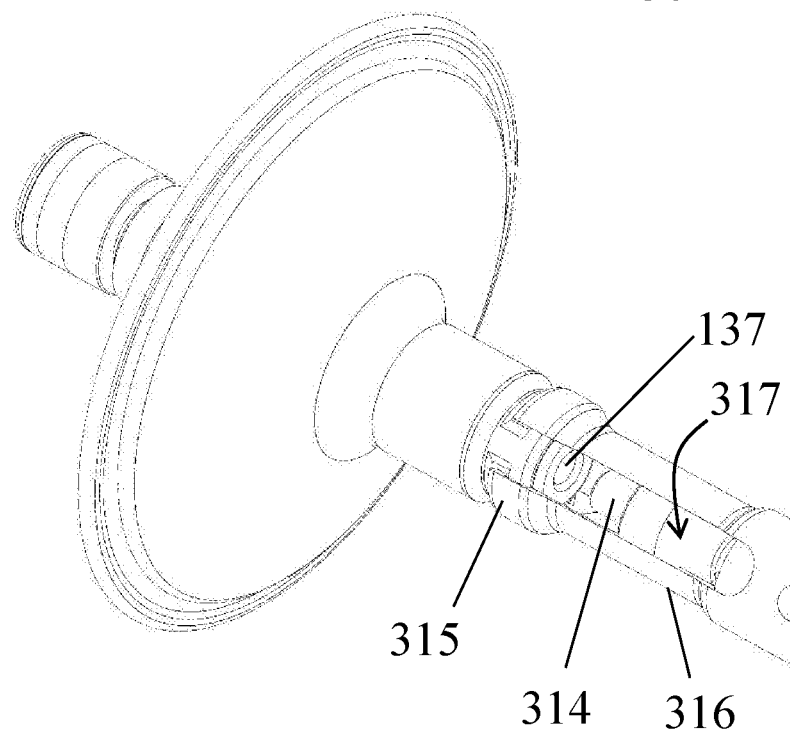
Figure 12C:
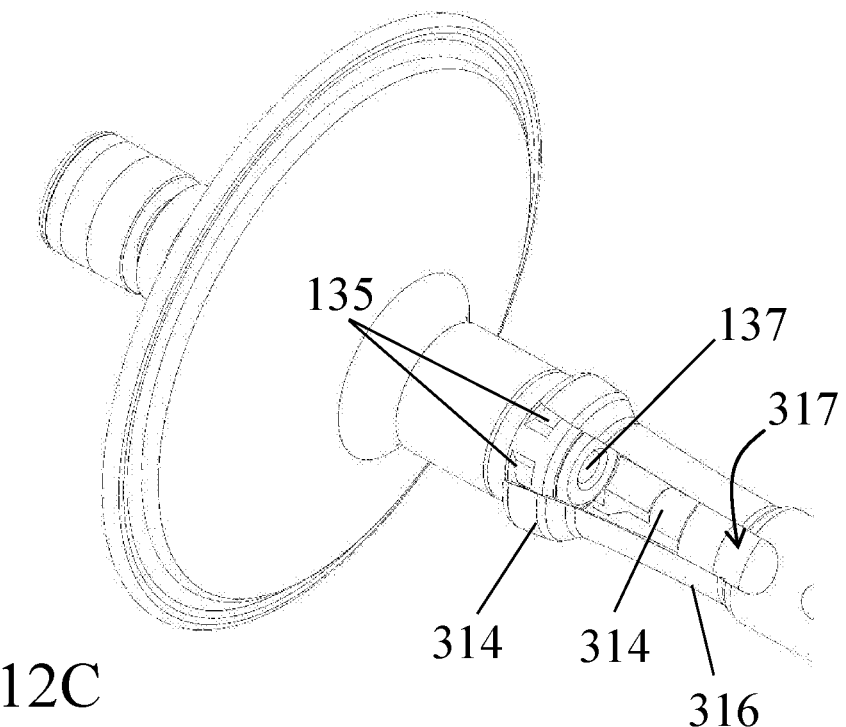
Figure 12D:
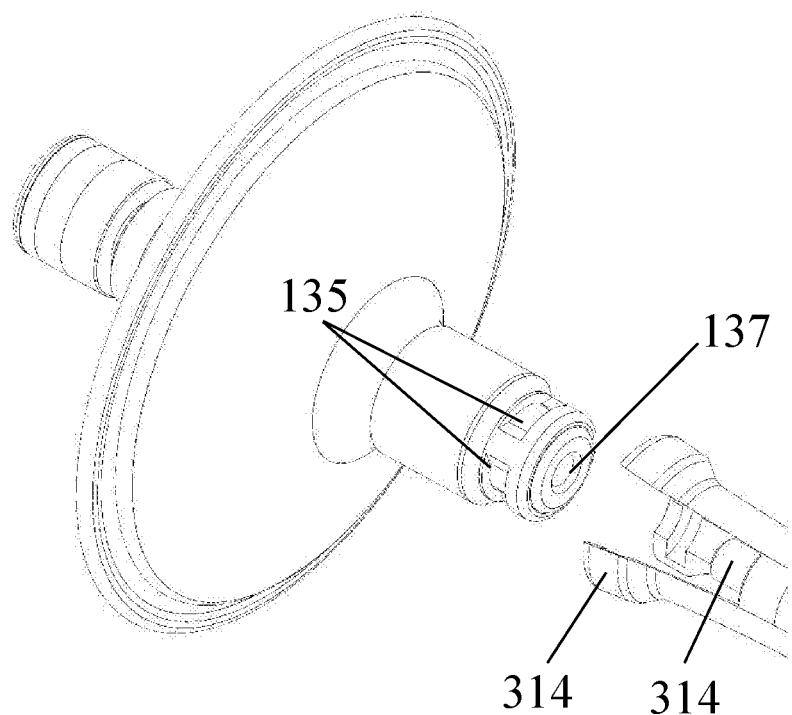

FIGS. 12A-12D are isometric views of implant deployment device 301 showing additional steps for disconnecting it from implant 100, for example. FIG. 12A shows implant deployment device 301 fully connected to implant 100 with inner connector 314 and outer connector 315. By unscrewing inner connector 314 from inner connectee (threading part 137) while hold outer connector 315 rotationally-fixed and firmly gripping onto outer connectee (recesses 135), outer connector 315 remains connected and inner connector 314 is disconnected, as shown in FIG. 12B. In order to then disconnect outer connector 315, its grasping jaws are shiftable from their normally closed form to an opened form, and this is achieved by pulling the now free inner member 311 relative to outer member 312 and pressing it against a lever mechanism in the outer connector that is arranged to thereby impose the grasping jaws to retract outwardly (as shown in FIG. 12C) so that implant deployment device 301 can be removed (FIG. 12D). The grasping jaws optionally include elastically bendable arms 316 angularly extending from outer member 312 to form such lever mechanism. Inner member 311 includes a widening 317 (located at a proximal portion inner connector 314 or proximally adjacent thereto) sized for forcing arms 316 to elastically bend from a first angle indicative of said closed form to a second angle indicative of said opened form. Widening 317 may be spheroidal with a narrowed portion thereof substantially mating to a collapsed concavity formable by arms 316 when the grasping jaws are in the closed form, and a widened portion thereof substantially mating to an enlarged concavity elastically formable by arms 316 when the grasping jaws are in said opened form.

The entire relative motion (pulling) of inner member 311 relative to outer member 312—first unscrewing from inner connectee and then forcing arms 316 to bend outwardly—is applicable, in this example, by revolving counterclockwise proximal knob 309. In some embodiments, implant deployment device 301 is configured such that proximal knob 309 cannot be revolved counterclockwise unless distal knob 308 is not fully revolved counterclockwise, as described above.

Figure 13A:
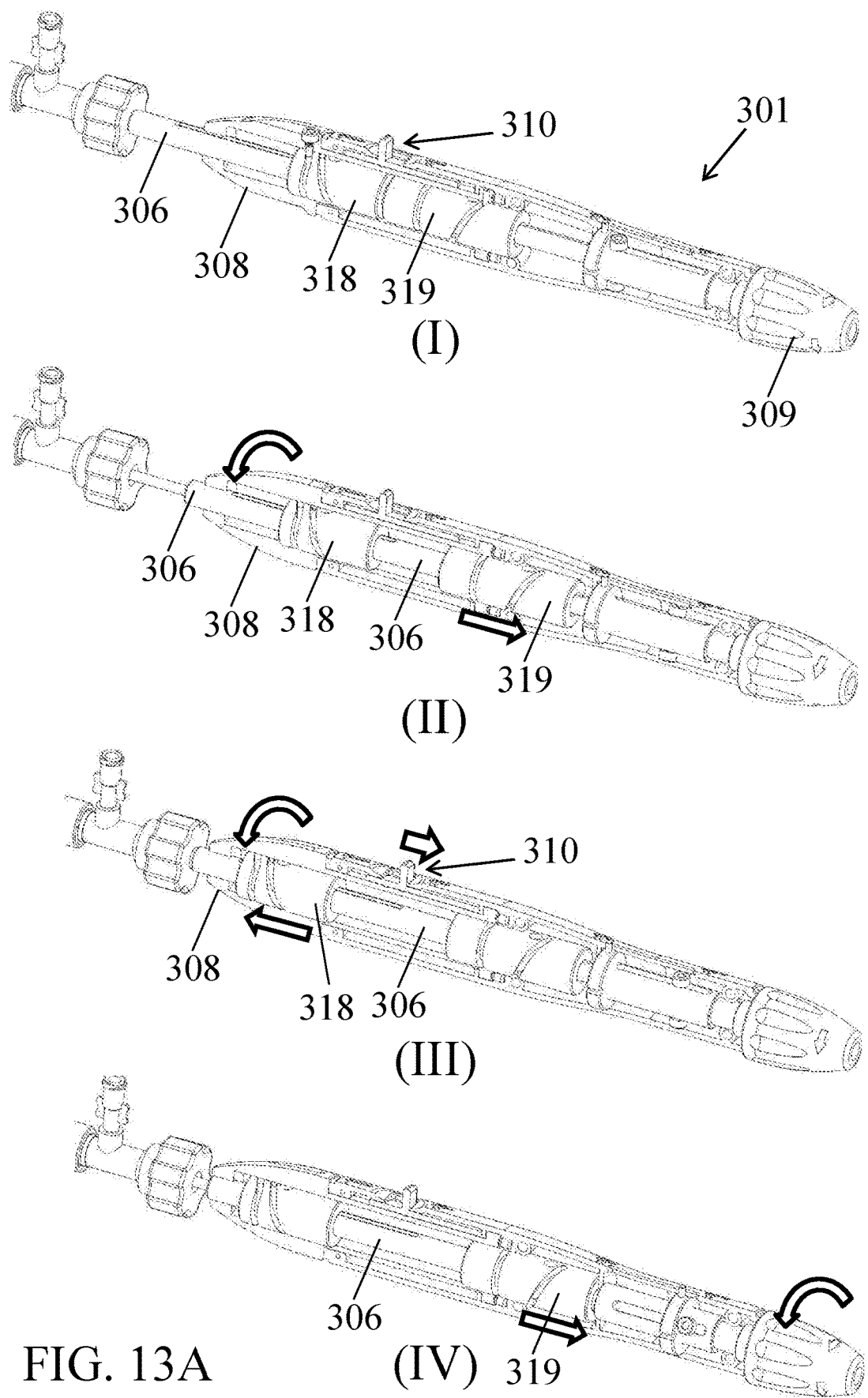
FIGS. 13A-13B are isometric views of exemplary mechanisms in an implant deployment device, in accordance with some embodiments of the invention.
Figure 13B:
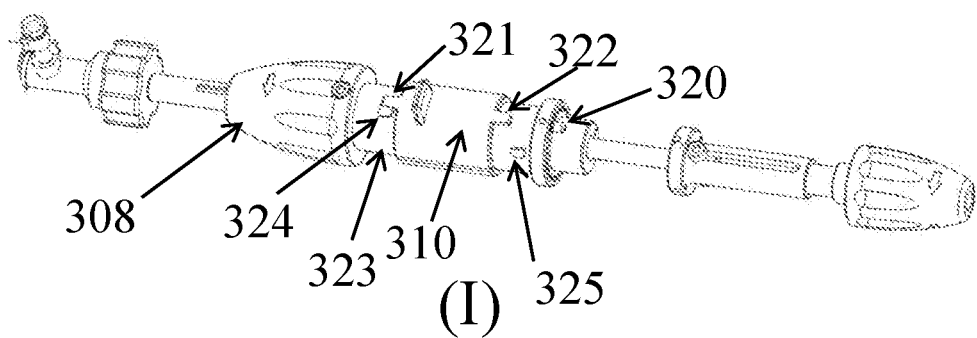
Figure 13B:
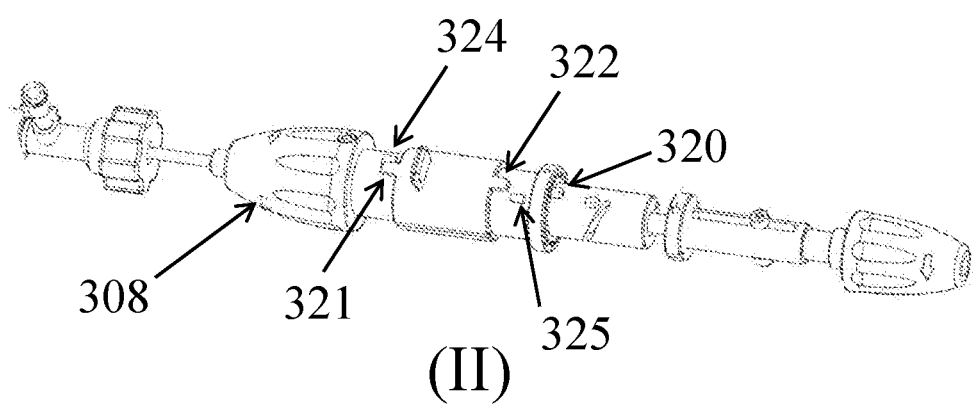
Figure 13B:
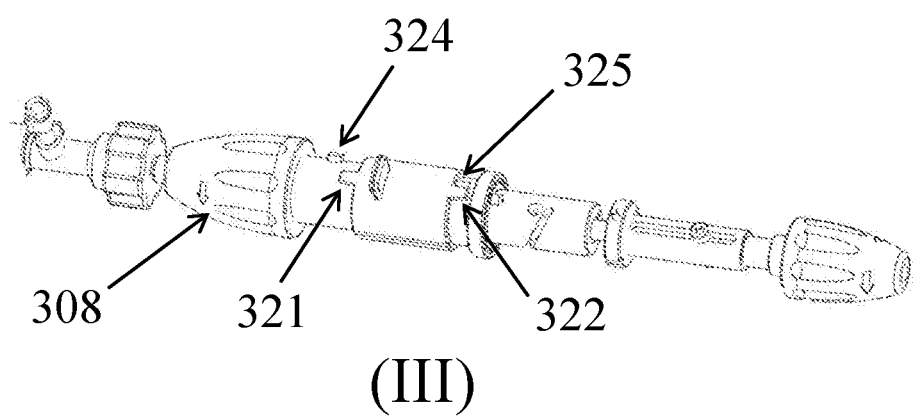
Figure 13B:
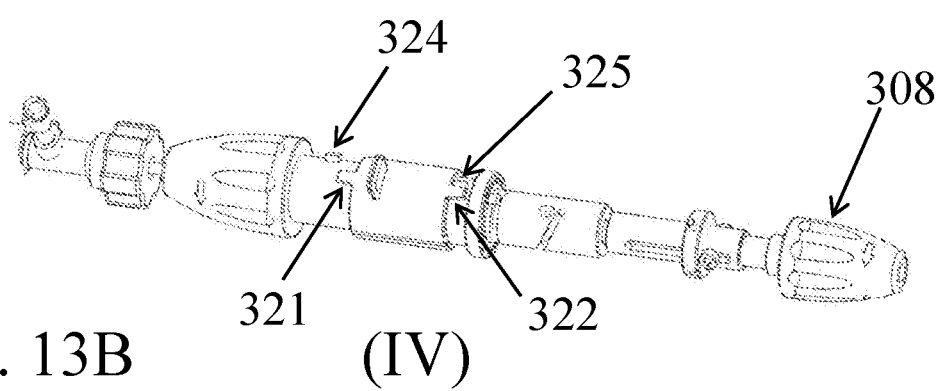

FIGS. 13A-13B are isometric views of exemplary mechanisms of implant deployment device 301 (encapsulated in handle 305) designed for enabling the described featured. A cam mechanism, linked with distal knob 308, includes a distal drum 318 and a proximal drum 319, separately rotatable around sheath spacer 306. Each drum has curved, partly helical, engraved passage, such that a pin 320 (rotatable with distal knob 308 revolving) can travel therein thereby forcing a one of drums 318 and 319 it engages to rotate and shift longitudinally according to engraved passage direction. Safety switch 310 operates a gear mechanism allowing the pin to shift from engaging with proximal drum 319 when switch 310 is at distal position, to engaging with distal drum 318 when switch 310 is at proximal position. An intermediate sleeve 323 is positioned concentrically between switch 310 and both drums 318 and 319, and is fixedly rotatable with distal knob 308 and freely rotatable about drums 318 and 319. Switch 310 includes a distal stop 321 and a proximal stop 322, and sleeve 323 includes a distal counter stop 324 and a proximal counter stop 325 distant from each other equally to the distance between distal stop 321 and proximal stop 322 plus allowed travel of switch 310.

As shown in FIGS. 13A(I)-(II) and 13B(I)-(II), safety switch 310 is in distal position. By revolving distal knob 308 counterclockwise, proximal drum 319 shifts in a proximal direction while distal drum 318 is kept in-place. Revolving of distal knob 308 is limited by distal counter stop 324 rotation from one side of distal stop 321 (FIG. 13B(I)) to other side of distal stop 321 (FIG. 13B(II)). Proximal drum 319 is fixedly connected to both inner member 311 and to sheath spacer 306 and distal drum 318 is fixedly connected to outer member 312. Therefore, proximal drum 319 pulls inner connector 314 relative to outer connector 315 (thus forcing folding of distal foldable unit 111) and sheath spacer 306 (thus facilitating retraction length L2), resulting in the transition from the devices arrangement demonstrated in FIGS. 10B and 11(II) to the devices arrangement demonstrated in FIGS. 10C and 11(III).

In order to further revolve distal knob 308 counterclockwise, switch 310 needs to be shifted to proximal position thus proximal stop 322 become engageable with proximal counter stop 325. As a results, distal knob 308 can be further revolved counterclockwise and is limited by proximal counter stop 325 rotation from one side of proximal stop 322 (FIG. 13B(II)) to other side of proximal stop 322 (FIG. 13B(III)).

As shown in FIGS. 13A(III) and 13B(III), safety switch 310 is in proximal position and distal drum 318 is shifted distally (further away from proximal drum 319) while proximal drum 319 is kept in-place. Therefore, distal drum 318 pushes outer connector 315 relative to inner connector 314 (thus forcing folding of proximal foldable unit 110), resulting in the transition from the devices arrangement demonstrated in FIGS. 10D and 11(IV) to the devices arrangement demonstrated in FIGS. 10E and 11(V).

Once distal knob 308 is fully revolved counterclockwise, the cam mechanism is further operational by revolving proximal knob 309, which controls detachment of implant deployment device 301 from implant 100 (continuously and sequentially) by first disconnecting inner connector 314 and then disconnecting outer connector 315, as previously described in more details. FIGS. 13A(IV) and 13B(IV) show cam mechanism arrangement after proximal knob 309 is fully rotated counterclockwise, thereby further rotating (thereby pulling) proximal drum 319 and inner member 311 with respect to outer member 312, resulting in the transition from the devices arrangement demonstrated sequentially from FIG. 12A to FIG. 12D.

According to some embodiments of the invention, the rigid implant body has a total length between 5 mm and 50 mm, optionally between 10 mm and 30 mm, optionally between 15 mm and 20 mm, optionally about 18 mm, and has a maximal outer diameter being about 5 mm or less, optionally about 3.5 mm or less, or optionally about 2 mm or less.

According to some embodiments of the invention, the griping sleeve (tubular skirt) 109 in its extended and narrowed form is about 25 mm to about 100 mm in length, optionally about 50 mm in length, and is sized for unhindered passage when constricted to a diameter of 2 to 4 mm, such as through a 12 French outer sheath 302/catheter (i.e., about 4 mm outer diameter) or/and is about 6 mm or less in diameter if not constricted. The septum opening is optionally substantially smaller than the outer sheath outer diameter but is elastically stretched wide when passing therethrough, optionally about 1 mm to about 3 mm (slit or puncture), optionally using formed using a 5 to 8 French (1.25 mm to 2.67 mm) trans-septal puncture kit. Tubular skirt 109 may be loaded into the outer sheath via a gradually constricting passage (e.g. via sheath loader 303), such as from about 7-10 mm down to 3.8-4.2 mm in diameter.

When in the (radially expanded) gripping form, the tubular skirt 109 may be less than about 25 mm, optionally about 15 mm or less in length, and about 10 mm or more, optionally about 15 mm or about 18 mm or more, in diameter. The tubular skirt 109 may be formed of a mesh having intertwined members (e.g., fibers, cords or the like), optionally made of metal (e.g., Ni—Ti alloy). In one exemplary embodiment the mesh includes 42 intertwined (one over one) Ni—Ti 100 micron fibers/cords Fiber diameter, optionally with light oxide surface finish, and 90-degree intersection angle.

Each of the following terms written in singular grammatical form: 'a', 'an', and 'the', as used herein, means 'at least one', or 'one or more'. Use of the phrase 'one or more' herein does not alter this intended meaning of 'a', 'an', or 'the'. Accordingly, the terms 'a', 'an', and 'the', as used herein, may also refer to, and encompass, a plurality of the stated entity or object, unless otherwise specifically defined or stated herein, or, unless the context clearly dictates otherwise. For example, the phrases: 'a unit', 'a device', 'an assembly', 'a mechanism', 'a component', 'an element', and 'a step or procedure', as used herein, may also refer to, and encompass, a plurality of units, a plurality of devices, a plurality of assemblies, a plurality of mechanisms, a plurality of components, a plurality of elements, and, a plurality of steps or procedures, respectively.

Each of the following terms: 'includes', 'including', 'has', 'having', 'comprises', and 'comprising', and, their linguistic/grammatical variants, derivatives, or/and conjugates, as used herein, means 'including, but not limited to', and is to be taken as specifying the stated component(s), feature(s), characteristic(s), parameter(s), integer(s), or step(s), and does not preclude addition of one or more additional component(s), feature(s), characteristic(s), parameter(s), integer(s), step(s), or groups thereof. Each of these terms is considered equivalent in meaning to the phrase 'consisting essentially of'.

Each of the phrases 'consisting of' and 'consists of', as used herein, means 'including and limited to'.

The phrase 'consisting essentially of', as used herein, means that the stated entity or item (system, system unit, system sub-unit, device, assembly, sub-assembly, mechanism, structure, component, element, or, peripheral equipment, utility, accessory, or material, method or process, step or procedure, sub-step or sub-procedure), which is an entirety or part of an exemplary embodiment of the disclosed invention, or/and which is used for implementing an exemplary embodiment of the disclosed invention, may include at least one additional 'feature or characteristic' being a system unit, system sub-unit, device, assembly, sub-assembly, mechanism, structure, component, or element, or, peripheral equipment, utility, accessory, or material, step or procedure, sub-step or sub-procedure), but only if each such additional 'feature or characteristic' does not materially alter the basic novel and inventive characteristics or special technical features, of the claimed entity or item.

The term 'method', as used herein, refers to steps, procedures, manners, means, or/and techniques, for accomplishing a given task including, but not limited to, those steps, procedures, manners, means, or/and techniques, either known to, or readily developed from known steps, procedures, manners, means, or/and techniques, by practitioners in the relevant field(s) of the disclosed invention.

Throughout this disclosure, a numerical value of a parameter, feature, characteristic, object, or dimension, may be stated or described in terms of a numerical range format. Such a numerical range format, as used herein, illustrates implementation of some exemplary embodiments of the invention, and does not inflexibly limit the scope of the exemplary embodiments of the invention. Accordingly, a stated or described numerical range also refers to, and encompasses, all possible sub-ranges and individual numerical values (where a numerical value may be expressed as a whole, integral, or fractional number) within that stated or described numerical range. For example, a stated or described numerical range 'from 1 to 6' also refers to, and encompasses, all possible sub-ranges, such as 'from 1 to 3', 'from 1 to 4', 'from 1 to 5', 'from 2 to 4', 'from 2 to 6', 'from 3 to 6', etc., and individual numerical values, such as '1', '1.3', '2', '2.8', '3', '3.5', '4', '4.6', '5', '5.2', and '6', within the stated or described numerical range of 'from 1 to 6'. This applies regardless of the numerical breadth, extent, or size, of the stated or described numerical range.

Moreover, for stating or describing a numerical range, the phrase 'in a range of between about a first numerical value and about a second numerical value', is considered equivalent to, and meaning the same as, the phrase 'in a range of from about a first numerical value to about a second numerical value', and, thus, the two equivalently meaning phrases may be used interchangeably. For example, for stating or describing the numerical range of room temperature, the phrase 'room temperature refers to a temperature in a range of between about 20° C. and about 25° C.', is considered equivalent to, and meaning the same as, the phrase 'room temperature refers to a temperature in a range of from about 20° C. to about 25° C.'.

The term 'about', as used herein, refers to ±10% of the stated numerical value.

It is to be fully understood that certain aspects, characteristics, and features, of the invention, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the invention which are illustratively described and presented in combination or sub combination in the context or format of a single embodiment, may also be illustratively described and presented in the context or format of a plurality of separate embodiments.

Although the invention has been described in conjunction with specific embodiments thereof, it is evident that many alternatives, modifications, and variations will be apparent to those skilled in the art. Accordingly, it is intended to embrace all such alternatives, modifications, and variations that fall within the spirit and broad scope of the appended claims.

All publications, patents, and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. A method for fixating an elongated implant across an organ wall in a subject's body, the method comprising:
    providing the implant attached to an implant deployment device, the implant comprising a rigid implant body enclosed with a compressible tubular skirt maintained stretched to an extended narrow form along said implant body;
    forming a wall opening in the organ wall;
    passing the implant through said wall opening until a chosen distal portion of said tubular skirt extends posteriorly beyond to the organ wall and a proximal portion of said tubular skirt remains anteriorly behind to the organ wall;
    while maintaining said tubular skirt proximal portion confined to said extended narrow form, compressing said tubular skirt distal portion to a first expanded form by at least partly regaining a first preformed shape of said tubular skirt distal portion;
    while maintaining said tubular skirt distal portion substantially in said first expanded form, compressing said tubular skirt proximal portion to a second expanded form by at least partly regaining a second preformed shape of said tubular skirt proximal portion; and
    detaching said implant from said implant deployment device,
    wherein said implant deployment device comprises a deployment device body comprising an inner member with an inner connector and an outer member with an outer connector, and wherein said providing the implant includes detachably connecting said inner connector to an inner connectee provided at a proximal end of said implant body and detachably connecting said outer connector to an outer connectee provided at a proximal end of said tubular skirt,
    wherein said detaching said implant from said implant deployment device includes separately and sequentially disconnecting said inner connector from said inner connectee and said outer connector from said outer connectee,
    wherein disconnecting said inner connector is followed by disconnecting said outer connector,
    wherein said outer connector is connectable to said outer connectee by means of a grasper arrangement, said grasper arrangement comprising grasping jaws configured for locking onto said outer connectee having a mating recess pattern, and said disconnecting said outer connector includes:
    after disconnecting said inner connector, forcing said grasping jaws to retract outwardly using said inner member.

2. The method of claim 1, wherein said passing the implant is first facilitated with an outer sheath sized to allow the implant passing thereinside and to maintain said tubular skirt constricted to said extended narrow form.

3. The method of claim 2, wherein said compressing said tubular skirt distal portion to said first expanded form is first facilitated by protruding the implant out of said outer sheath such that said tubular skirt distal portion is unconstricted by said outer sheath and said tubular skirt proximal portion remains constricted by said outer sheath.

4. The method of claim 2, wherein said compressing said tubular skirt proximal portion to said second expanded form is first facilitated by further protruding the implant out of said outer sheath such that both said tubular skirt distal portion and said tubular skirt proximal portion are unconstricted by said outer sheath.

5. The method of claim 1, wherein said tubular skirt comprises a flexible gripping sleeve, wherein a distal end of the flexible gripping sleeve is fixedly connected to a distal periphery of said implant body and a proximal end of the flexible gripping sleeve is slidably connected to said implant body along a path extending proximally to said distal periphery.

6. The method of claim 5, wherein said method further comprises:
    gripping against opposing ends of the organ wall around said implant body, with said tubular skirt distal portion compressed to said first expanded form and said tubular skirt proximal portion compressed to said second expanded form, with sufficient force to maintain said implant body aligned across the organ wall.

7. The method of claim 5, wherein said flexible gripping sleeve has a preformed bellows-like structure with foldable units, including a proximal foldable unit comprising said tubular skirt proximal portion and a distal foldable unit comprising said tubular skirt distal portion, connected one with the other directly or with a non-foldable spacing unit therebetween for spacing sized to compensate for width of said organ wall.

8. The method of claim 7, wherein said gripping against opposing ends of the organ wall includes:
    forcing said proximal foldable unit into forming a proximal wing extending outwardly-radially relative to said implant body, so as to form a first proximal surface and a second proximal surface interconnected with a proximal edge, and
    forcing said distal foldable unit into forming a distal wing extending outwardly-radially relative to said implant body, so as to form a first distal surface and a second distal surface interconnected with a distal edge.

9. The method of claim 1, wherein said compressing said tubular skirt proximal portion includes:
    pulling said implant body so as to press said tubular skirt distal portion in said first expanded form against said organ wall until reaching a chosen shaping of said tubular skirt distal portion or a chosen resistance magnitude developable by said organ wall in response to said pulling.

10. The method of claim 1, wherein said providing the implant includes constricting said tubular skirt in said extended narrow form with constricting means.

11. The method of claim 1, wherein said stretching said tubular skirt to said extended narrow form is facilitated by relatively positioning said outer connector or said inner connector at a first connecting distance therebetween.

12. The method of claim 1, wherein said compressing said tubular skirt distal portion to said first expanded form is facilitated by relatively positioning said outer connector or said inner connector at a second connecting distance therebetween.

13. The method of claim 12, wherein said compressing said tubular skirt proximal portion to said second expanded form is facilitated by relatively positioning said outer connector or said inner connector at a third connecting distance therebetween.

14. The method of claim 13, wherein shifting from said second connecting distance to said third connecting distance is applicable only upon releasing a first safety.

15. The method of claim 14, wherein said first safety is releasable only when said outer connector is positioned at said second connecting distance relative to said inner connector.

16. The method of claim 1, wherein said inner connector is connectable to said inner connectee by means of a screw arrangement and said disconnecting said inner connector includes:
  holding said outer connectee rotationally fixed with said outer connector; and
  revolving, clockwise or counterclockwise, said inner connector relative to said inner connectee until unscrewing said inner connector.

17. The method of claim 1, wherein said compressing said tubular skirt distal portion or said compressing said tubular skirt proximal portion includes allowing said tubular skirt to at least partly conform to outer boundaries of said implant body and of the organ wall.

* * * * *